US005489499A

United States Patent [19]
Yumoto

[11] Patent Number: 5,489,499
[45] Date of Patent: Feb. 6, 1996

[54] PHOTOSENSITIVE TRIHALOMETHYL-S-TRIAZINE COMPOUND AND PHOTOPOLYMERIZABLE COMPOSITION

[75] Inventor: Masatoshi Yumoto, Shizuoka, Japan

[73] Assignee: Fuji Photo Film Co., Ltd., Kanagawa, Japan

[21] Appl. No.: 329,646

[22] Filed: Oct. 25, 1994

[30] Foreign Application Priority Data

Oct. 26, 1993 [JP] Japan ................................. 5-267541

[51] Int. Cl.$^6$ ............................. G03C 1/725; G03F 7/05
[52] U.S. Cl. ...................... 430/281.1; 430/919; 430/920; 522/52; 522/63
[58] Field of Search ................................. 430/281, 919, 430/920; 522/52, 63

[56] References Cited

U.S. PATENT DOCUMENTS

| | | | |
|---|---|---|---|
| 3,954,475 | 5/1976 | Bonham et al. | 260/248 |
| 3,987,037 | 10/1976 | Bonham et al. | 430/281 |
| 4,189,323 | 2/1980 | Buhr | 430/281 |
| 4,505,793 | 3/1985 | Tamoto et al. | 430/281 |
| 4,774,163 | 9/1988 | Higashi | 430/281 |
| 4,837,128 | 6/1989 | Kawamur et al. | 430/281 |
| 4,937,161 | 6/1990 | Kita et al. | 430/281 |
| 4,987,055 | 1/1991 | Rode et al. | 430/281 |
| 5,059,511 | 10/1991 | Higashi et al. | 430/281 |
| 5,202,361 | 4/1993 | Zimmermann et al. | 522/170 |

Primary Examiner—John C. Bleutge
Assistant Examiner—Randy Gulakowski
Attorney, Agent, or Firm—Sughrue, Mion, Zinn, Macpeak & Seas

[57] ABSTRACT

A photosensitive trihalomethyl-s-triazine compound and a photopolymerizable composition containing the photosensitive trihalomethyl-s-triazine compound. The photosensitive trihalomethyl-s-triazine compound is represented by formula (I):

wherein X represents a chlorine atom or a bromine atom; Y represents an alkyl group, a $CF_3$ group, a $CF_2Cl$ group, an alkyl group substituted with a group or an atom other than hydrogen atoms, a $C_6F_5$ group, or a group represented by $-Z-CO-OR^3$ or $-C_6H_4-R^4$, in which $R^3$ represents a hydrogen atom or alkyl group, Z represents $-C_2H_4-$, $-C_3H_6-$, $-CH=CH-$, or o-phenylene group, and $R^4$ represents a hydrogen atom, a hydroxyl group, an alkyl group, a substituted alkyl group, an aryl group, an alkoxy group, a substituted alkoxy group, a halogen atom, an alkoxycarbonyl group, a cyano group, an acyl group, a nitro group, a formyl group, a mercapto group, an alkylthio group, or a dialkylamino group; $R^1$ and $R^2$ each independently represent a hydrogen atom, a hydroxyl group, an alkyl group, an aryl group, an alkoxy group, a substituted alkoxy group, an acyloxy group, a halogen atom, an alkoxycarbonyl group, a cyano group, a nitro group, a carboxyl group, or a group represented by formula (II) or (III):

wherein $R^5$ and $R^6$ each independently represent a hydrogen atom, an alkyl group, a substituted alkyl group, or a substituted aryl group, wherein $R^7$ and $R^8$ each independently represent a hydrogen atom, an alkyl group, a substituted alkyl group, an aryl group, a substituted aryl group, or an acyl group, and wherein $R^5$ and $R^7$ may be connected to $R^6$ and $R^8$ respectively, to form a ring.

2 Claims, No Drawings

PHOTOSENSITIVE TRIHALOMETHYL-S-TRIAZINE COMPOUND AND PHOTOPOLYMERIZABLE COMPOSITION

FIELD OF THE INVENTION

The present invention relates to a novel compound useful in the field of recording materials such as a photosensitive protective layer, a printing plate, a photoresist and a proof, which produces a free radical upon exposure to light and a photopolymerizable composition containing the same. More particularly, the present invention relates to a novel photosensitive trihalomethyl-s-trizine compound and a photopolymerizable composition containing the same.

BACKGROUND OF THE INVENTION

A compound which undergoes decomposition upon exposure to light to produce a free radical (free radical generator) is well known in the field of the graphic arts, photosensitive recording materials, etc. It has wide application as a radical photopolymerization initiator incorporated in a photopolymerizable composition, a light activator incorporated in a free radical-containing photographic composition, a photoinitiator for a reaction catalyzed by an acid generated upon exposure to light, or the like. Such a free radical generator has been used to prepare a variety of photosensitive materials useful in printing, duplicating, copying and other recording material systems.

Bis(trihalomethyl)-s-triazine compounds have been proposed as free halogen radical generators which are sensitive to light of a wavelength ranging from the near ultraviolet region to the visible light range. These compounds are further described in U.S. Pat. Nos. 3,954,475, 3,987,037, 4,189,323, 4,696,888, 4,837,128, JP-A-62-58241 JP-A-2-149570 (The term "JP-A" as used herein means an "unexamined published Japanese patent application"), etc. Though sensitive to light of a wavelength ranging from the near ultraviolet region to the visible light range, these compounds are disadvantageous in that the products of decomposition by exposure are liable to have light yellow coloration. These compounds are also disadvantageous in that when used in a system where a radical photopolymerization initiator or its decomposition products remain in the recording layer, the recording layer becomes yellow in color due to the decomposition of the residual compounds by exposure to light during storage in bright places. The inventors made extensive studies to overcome these problems. As a result, it has been found that the compound according to the present invention exhibits excellent properties.

In connection with the compound according to the present invention, JP-A-58-40302 discloses a compound represented by formula (IV):

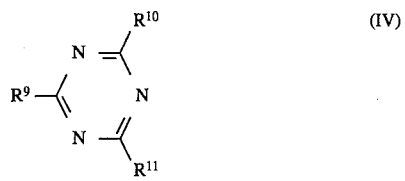

wherein $R^9$, $R^{10}$ and $R^{11}$ each represent an alkyl, aryl, alkenyl or piperidino group which may have substituents, $-NR_2$, $-OR$ or $-SR$, in which R represents a hydrogen atom or an alkyl group, with the proviso that at least one of $R^9$, $R^{10}$ and $R^{11}$ represents a monohalogen-, dihalogen- or trihalogen-substituted methyl group.

In specific examples of the compound and the examples, however, only monohalogen-, dihalogen- or trihalogen-substituted methyl groups having two or three halogen substituents on one triazine ring are disclosed. Only chlorine atoms and bromine atoms are disclosed as halogen substituents. No examples of the compound having a fluorine atom substituent are disclosed. Of course, there is no reference to the interesting properties of a photosensitive s-triazine compound having one trichloromethyl group or tribromomethyl group according to the present invention.

SUMMARY OF THE INVENTION

It is an object of the present invention to provide a photosensitive trihalomethyl-s-triazine compound sensitive to light of a wavelength ranging from the near ultraviolet region to the visible light range which exhibits a high sensitivity and is insusceptible to coloration of the products of decomposition by exposure to light and storage in bright places, and a photopolymerizable composition comprising the same.

The foregoing and other objects of the present invention will become more apparent from the following detailed description and examples.

The foregoing object of the present invention is accomplished with a photosensitive s-triazine compound having one trichloromethyl group or tribromomethyl group represented by formula (I):

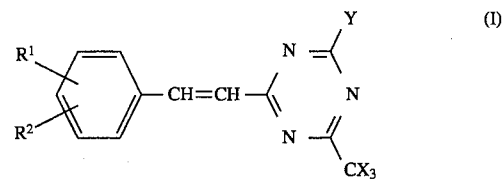

wherein x represents a chlorine atom or a bromine atom; Y represents an alkyl group, a $CF_3$ group, a $CF_2Cl$ group, an alkyl group substituted with a group or an atom other than hydrogen atoms, a $C_6F_5$ group, or a group represented by $-Z-CO-OR^3$ or $-C_6H_4-R^4$, in which $R^3$ represents a hydrogen atom or alkyl group, Z represents $-C_2H_4-$, $-C_3H_6-$, $-CH=CH-$, or o-phenylene group, and $R^4$ represents a hydrogen atom, a hydroxyl group, an alkyl group, a substituted alkyl group, an aryl group, an alkoxy group, a substituted alkoxy group, a halogen atom, an alkoxycarbonyl group, a cyano group, an acyl group, a nitro group, a formyl group, a mercapto group, an alkylthio group, or a dialkylamino group; $R^1$ and $R^2$ each independently represent a hydrogen atom, a hydroxyl group, an alkyl group, an aryl group, an alkoxy group, a substituted alkoxy group, an acyloxy group, a halogen atom, an alkoxycarbonyl group, a cyano group, a nitro group, a carboxyl group, or a group represented by formula (II) or (III):

wherein $R^5$ and $R^6$ each independently represent a hydrogen atom, an alkyl group, a substituted alkyl group, or a substituted aryl group,

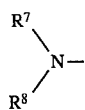

(III)

wherein $R^7$ and $R^8$ each independently represent a hydrogen atom, an alkyl group, a substituted alkyl group, an aryl group, a substituted aryl group, or an acyl group, and wherein $R^8$ and $R^7$ may be connected to $R^6$ and $R^8$, respectively, to form a ring.

DETAILED DESCRIPTION OF THE INVENTION

In formula (I), the alkyl group represented by Y preferably has 1 to 16 carbon atoms, particularly 1 to 10 carbon atoms. The alkyl group represented by $R^3$ preferably has 1 to 8 carbon atoms, particularly 1 to 4 carbon atoms. The alkyl group represented by $R^4$ preferably has 1 to 8 carbon atoms, particularly 1 to 4 carbon atoms. The alkoxy group represented by $R^4$ or the alkoxy group in the alkoxycarbonyl group represented by $R^4$ preferably has 1 to 8 carbon atoms, particularly 1 to 4 carbon atoms. The aryl group represented by $R^4$ preferably has 6 to 14 carbon atoms, particularly 6 to 10 carbon atoms. The alkylthio group represented by $R^4$ preferably has 1 to 16 carbon atoms, particularly 1 to 8 carbon atoms.

In formula (I), examples of the substituent other than hydrogen atoms on the alkyl group represented by Y include an aryl group, a substituted aryl group, a hydroxyl group, an alkoxy group, a carboxyl group, an alkoxycarbonyl group, an aryloxycarbonyl group, a cyano group, an acyl group, a nitro group, a mercapto group, an alkylthio group, an arylthio group, or a dialkylamino group. Among these, preferred examples thereof include an aryl group having 6 to 10 carbon atoms, which is substituted with a hydroxyl group, an aryl group having 6 to 10 carbon atoms, an alkoxy group having 1 to 8 carbon atoms, or a dialkylamino group having 1 to 8 carbon atoms; a hydroxyl group; an alkoxy group having 1 to 8 carbon atoms; an alkoxycarbonyl group having 1 to 4 carbon atoms; a cyano group; a mercapto group; an alkylthio group having 1 to 8 carbon atoms; an arylthio group having 6 to 10 carbon atoms; or a dialkylamino group having 1 to 8 carbon atoms.

In formula (I), examples of the substituent on the substituted alkyl group and the substituted alkoxy group represented by $R^4$ include an aryl group, a halogen atom, an alkoxy group, a carboxyl group, an alkoxycarbonyl group, an aryloxycarbonyl group, a cyano group, an acyl group, a nitro group, or a dialkylamino group. Among these, preferred examples thereof include a halogen atom, an alkoxy group having 1 to 8 carbon atoms, an alkoxycarbonyl group having 1 to 8 carbon atoms, a carboxyl group, a cyano group, or an acyl group.

In formula (I), the alkyl group represented by $R^1$ or $R^2$ preferably has 1 to 16 carbon atoms, particularly 1 to 8 carbon atoms. The aryl group represented by $R^1$ or $R^2$ preferably has 6 to 14 carbon atoms, particularly 6 to 10 carbon atoms.

In formula (I), the alkoxy group represented by $R^1$ or $R^2$ or the alkoxy group in the alkoxycarbonyl group represented by $R^1$ or $R^2$ preferably has 1 to 18 carbon atoms, particularly 1 to 8 carbon atoms.

In formula (I), examples of the substituents on the substituted alkoxy group represented by $R^1$ or $R^2$ include a hydroxyl group, an aryl group, a halogen atom, an alkoxy group, a carboxyl group, an alkoxycarbonyl group, an aryloxycarbonyl group, a cyano group, an acyl group, a nitro group, and a dialkylamino group. Particularly preferred among them is a $C_{1-8}$ alkoxy group, an alkoxycarbonyl group, a carboxyl group, a cyano group, or an acyl group.

In formulae (II) and (III), the alkyl group represented by $R^5$, $R^6$, $R^7$ or $R^8$ preferably has 1 to 16 carbon atoms, particularly 1 to 8 carbon atoms. The alkyl group represented by $R^5$, $R^6$, $R^7$ or $R^8$ preferably has 6 to 14 carbon atoms, particularly 6 to 10 carbon atoms.

In formulae (II) and (III), examples of the substituents on the substituted alkyl group represented by $R^5$, $R^6$, $R^7$ or $R^8$ include an aryl group, a halogen atom, an alkoxy group, a carboxyl group, an alkoxycarbonyl group, an aryloxycarbonyl group, a cyano group, an acyl group, a nitro group, and a dialkylamino group.

Other examples of the substituents on the substituted aryl group represented by $R^5$, $R^6$, $R^7$ or $R^8$ include an alkyl group.

Particularly preferred among the substituents on the substituted alkyl and aryl groups represented by $R^5$, $R^6$, $R^7$ or $R^8$ is a halogen atom, a carboxyl group, or a $C_{1-8}$ alkoxycarbonyl group, a cyano group, or an acyl group.

Examples of the ring formed by the connection of $R^5$ to $R^6$ and/or $R^7$ to $R^6$ include those represented by formulae (A) to (J):

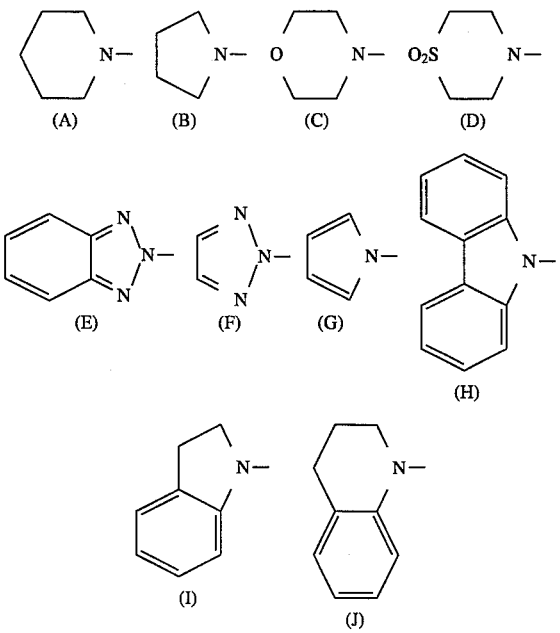

Particularly preferred among the compounds represented by formula (I) is one wherein X is a chlorine atom, Y is a methyl group, an ethyl group, a propyl group, a butyl group, a pentyl group, a hexyl group, a decyl group, a $CF_3$ group, a $CF_2Cl$ group, a benzyl group, a diphenylmethyl group, a triphenylmethyl group, a p-methoxybenzyl group, a p-diethylaminobenzyl group, a hydroxymethyl group, a methoxymethyl group, a methoxypropyl group, a cyanomethyl group, a dimethylaminomethyl group, a diethylaminopropyl group, a mercaptomethyl group, a methylthiomethyl group, a phenylthiomethyl group, a carboxylethyl group, a methoxycarbonylethyl group, a methoxycarbonylpropyl group, a methoxycarbonylethenyl group, a $C_6F_5$ group, a phenyl group, a tolyl group, a p-fluorophenyl group, a p-chlorophenyl group, a p-trifluoromethylphenyl group, an o-trifluoromethylphenyl group, a p-trichloromethylphenyl group, a p-methoxyphenyl group, a p-ethoxyphenyl group, a p-methoxyethoxyphenyl group, an o-methoxycarbonylmethoxy group, a p-cyanophenyl group, a p-nitrophenyl group, an o-mercaptophenyl group, a p-methylthiophenyl group, or a p-diethylaminophenyl group, and $R^1$ and $R^2$ each independently represent a hydrogen atom, a hydroxyl group, a halogen atom, a methyl group, an ethyl group, a propyl group, a methoxy group, an ethoxy group, a propoxy group, a butoxy group, a methoxycarbonylmethoxy group, an ethoxycarbonylmethoxy group, a cyanomethoxy group, a cyanoethoxy group, an acetoxy group, a benzoyloxy group, a hydroxyethoxy group, a bromoethoxy group, a chloroethoxy group, a bromopropoxy group, a chloropropoxy group, a phenylaminocarbonyl group, an anisylaminocarbonyl group, a diphenylaminocarbonyl group, a dianisylaminocarbonyl group, a dimethylaminocarbonyl group, a diethylaminocarbonyl group, an acetylamino group, or a benzoylamino group. Particularly preferably, Y in formula (I) represents a $CF_3$ group.

Examples of compounds which can be used as photosensitive trihalomethyl-s-triazine compounds will be given below, but the present invention should not be construed as being limited thereto.

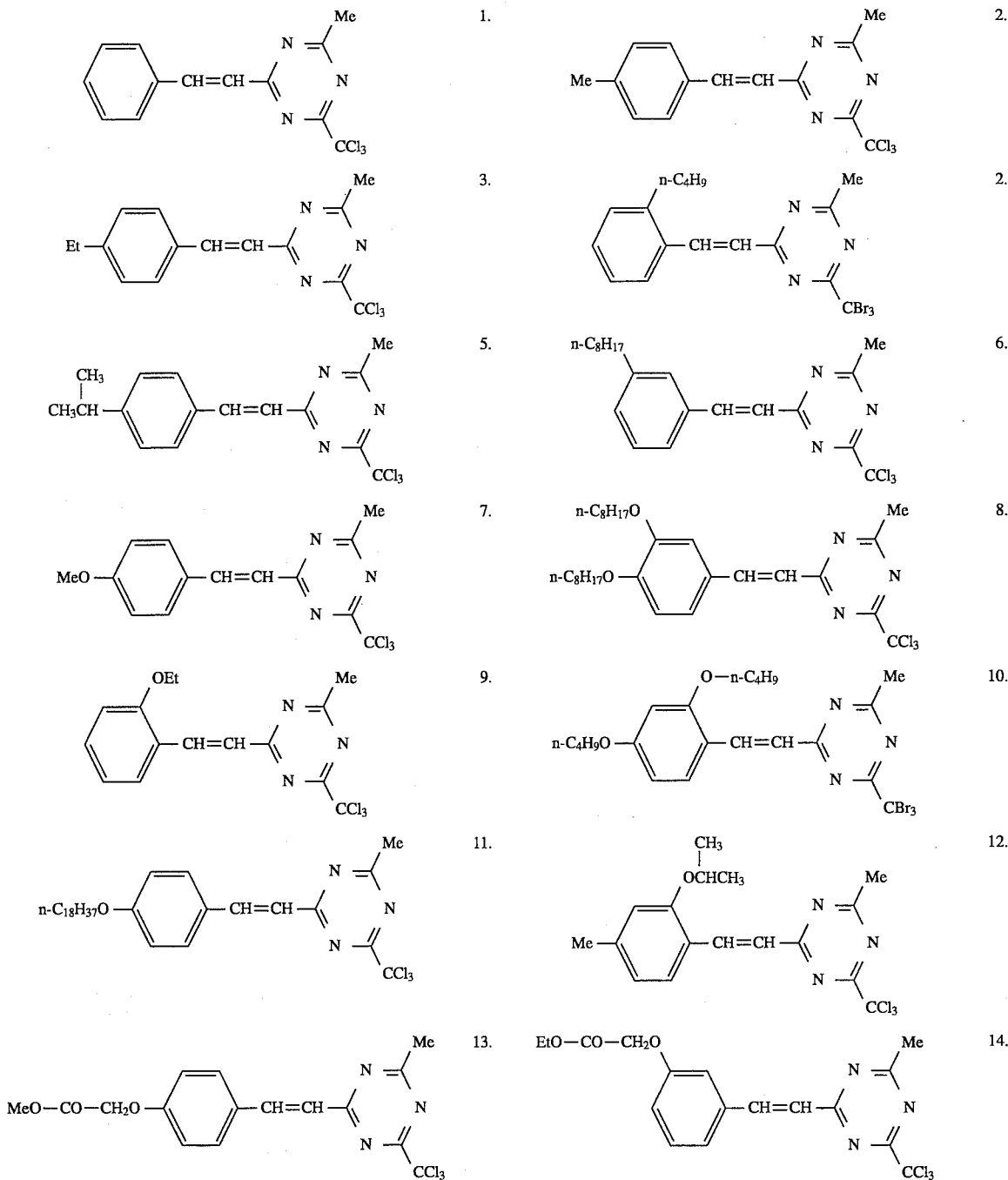

-continued
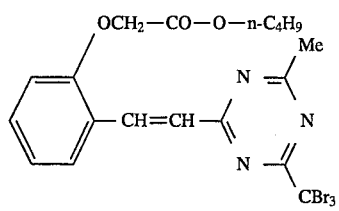 15.
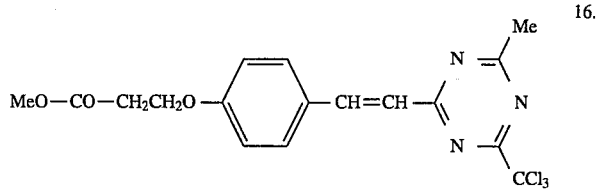 16.
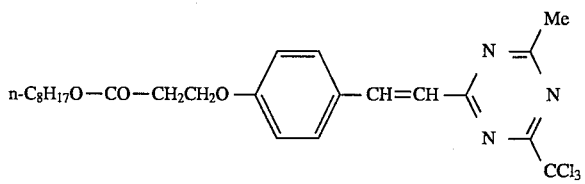 17.
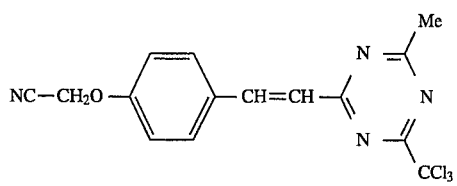 18.
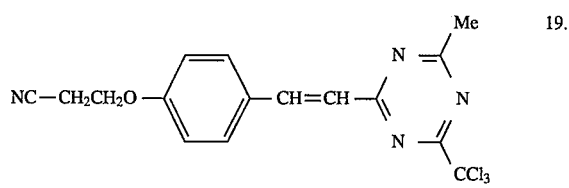 19.
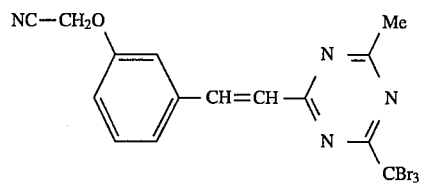 20.
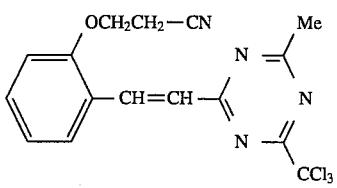 21.
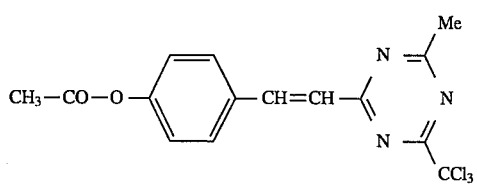 22.
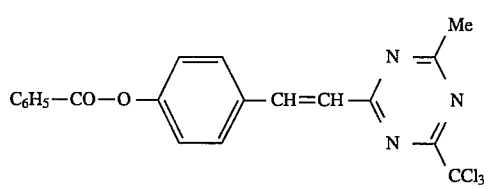 23.
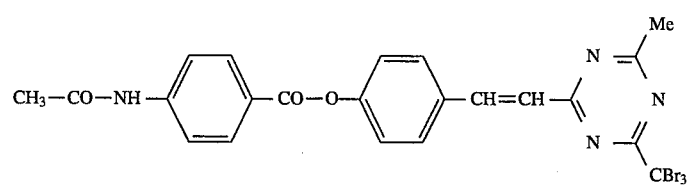 24.
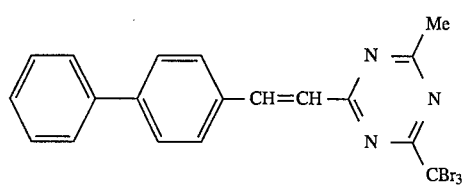 25.
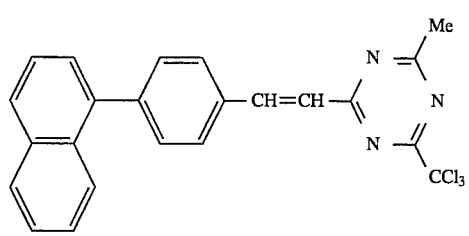 26.
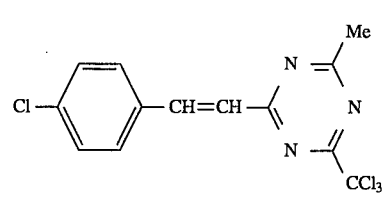 27.
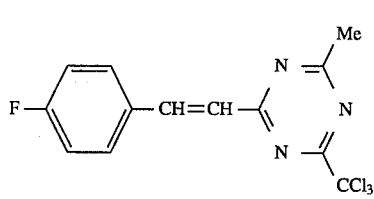 28.

-continued 29. 3-Br-C6H4-CH=CH- triazine(Me, CCl3)

30. 4-MeO-CO-C6H4-CH=CH- triazine(Me, CBr3)

31. 4-NC-C6H4-CH=CH- triazine(Me, CCl3)

32. 4-O2N-C6H4-CH=CH- triazine(Me, CCl3)

33. 4-HO-CO-C6H4-CH=CH- triazine(Me, CCl3)

34. 4-MeNH-CO-C6H4-CH=CH- triazine(Me, CBr3)

35. 4-Me2N-CO-C6H4-CH=CH- triazine(Me, CCl3)

36. 4-(n-C4H9)2N-CO-C6H4-CH=CH- triazine(Me, CCl3)

37. 4-Me(n-C8H17)N-CO-C6H4-CH=CH- triazine(Me, CCl3)

38. 4-Et(MeO-CO-CH2)N-CO-C6H4-CH=CH- triazine(Me, CCl3)

39. 3-(n-C8H17)2N-CO-C6H4-CH=CH- triazine(Me, CCl3)

40. 4-C6H5-NH-CO-C6H4-CH=CH- triazine(Me, CCl3)

41. 4-(C6H5)2N-CO-C6H4-CH=CH- triazine(Me, CCl3)

42. 4-(p-MeO-C6H4)2N-CO-C6H4-CH=CH- triazine(Me, CCl3)

43. 4-(morpholino-CO)-C6H4-CH=CH- triazine(Me, CCl3)

44. 4-(piperidino-CO)-C6H4-CH=CH- triazine(Me, CBr3)

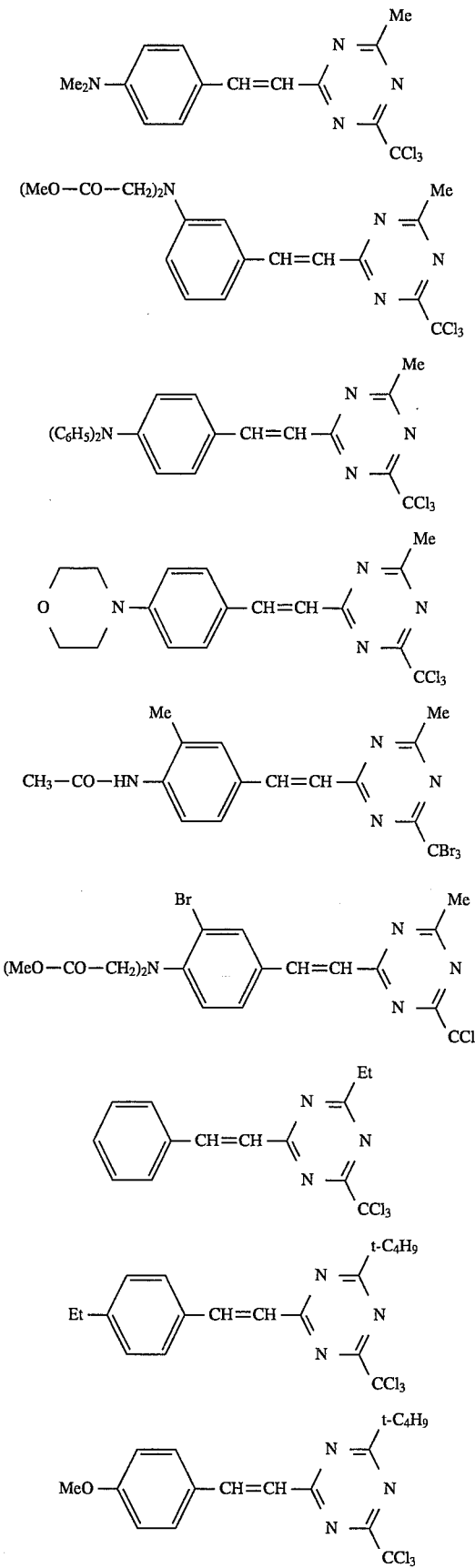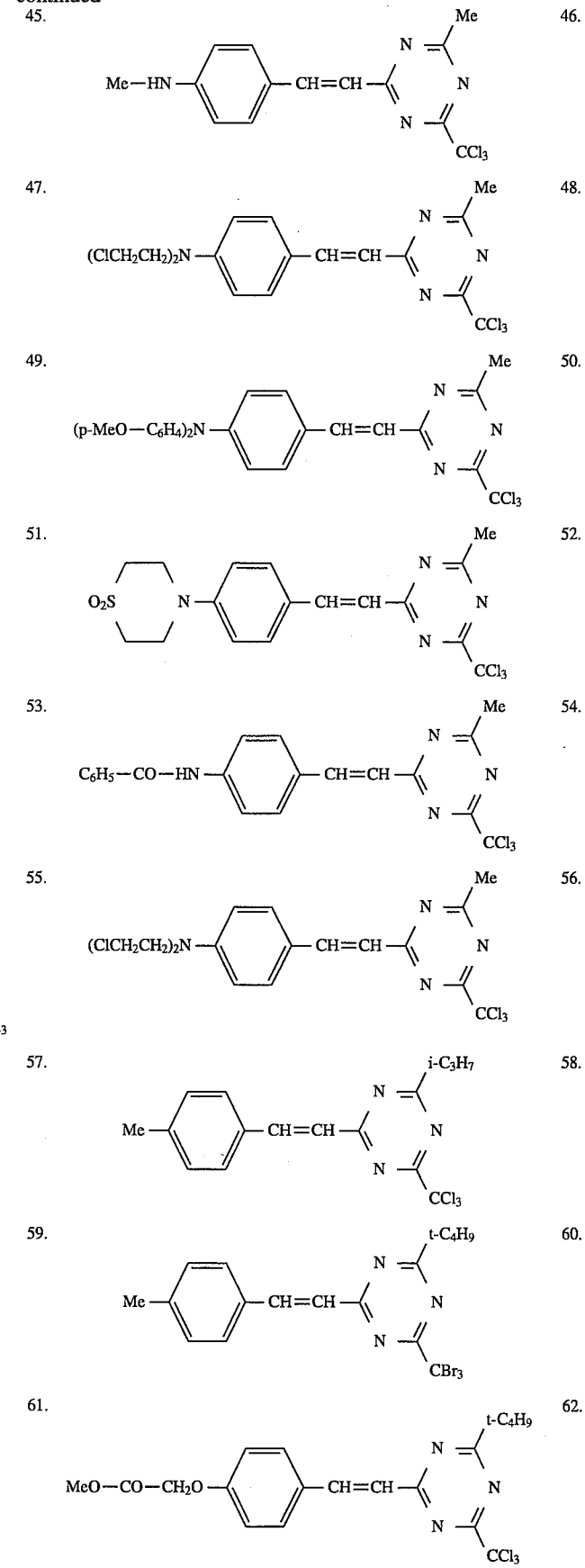

-continued
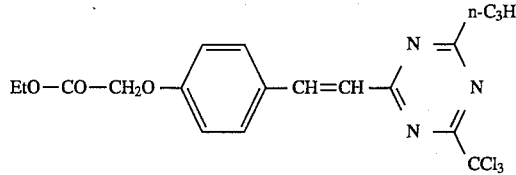
63.
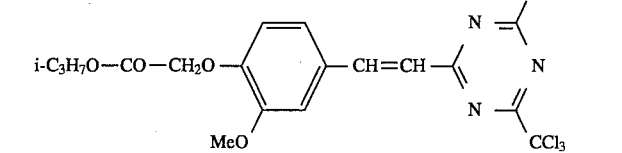
64.
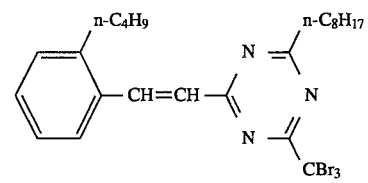
65.
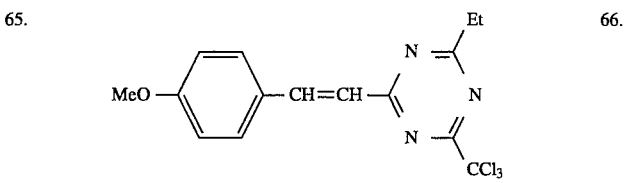
66.
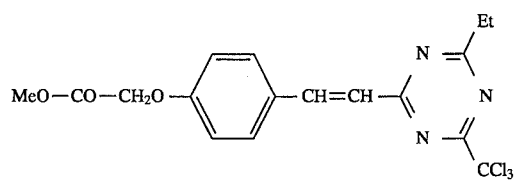
67.
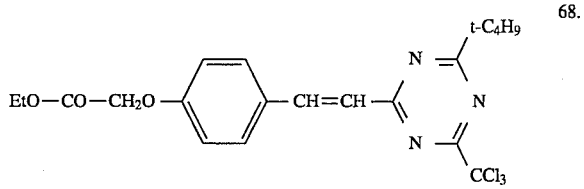
68.
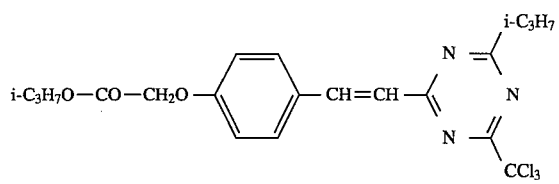
69.
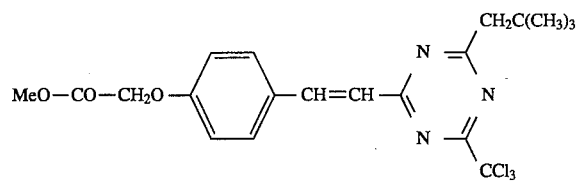
70.
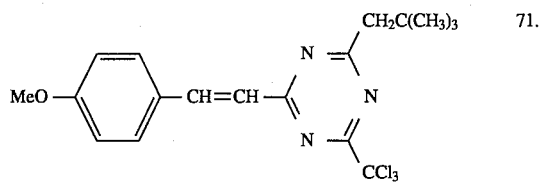
71.
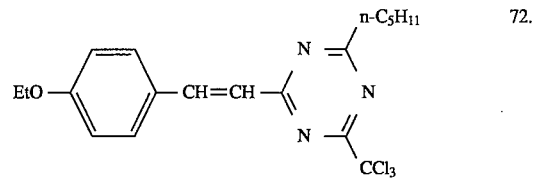
72.
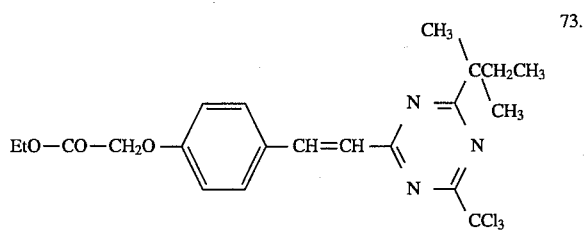
73.
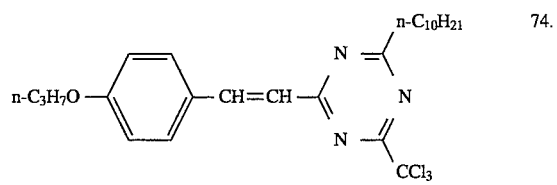
74.
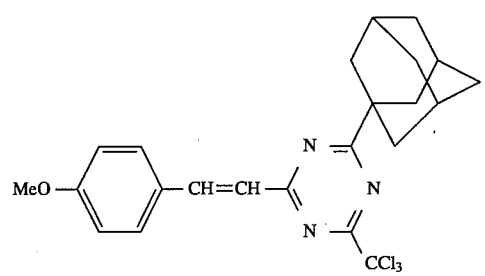
75.

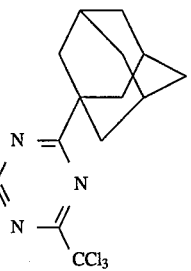
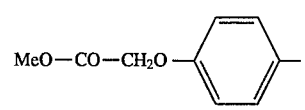
76.
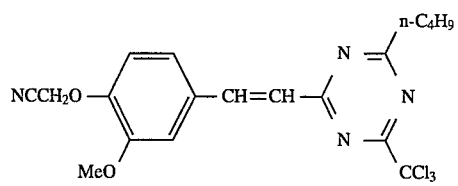
77.
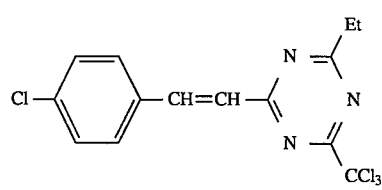
78.
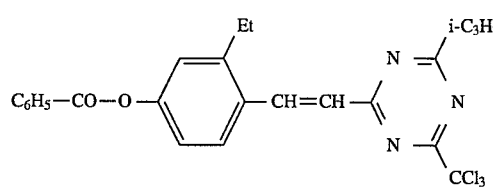
79.
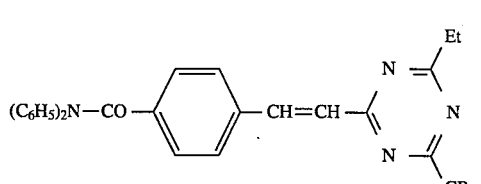
80.
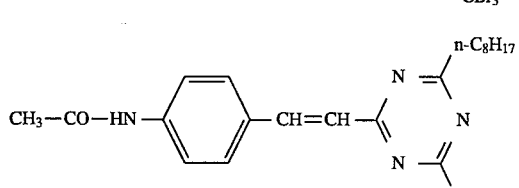
81.
82.
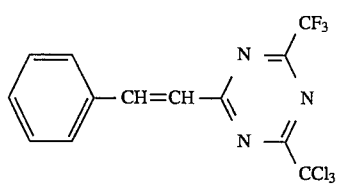
83.
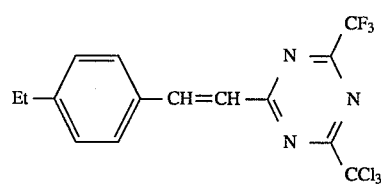
84.
85.
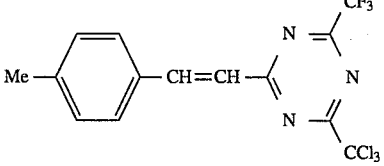
86.
87.
88.
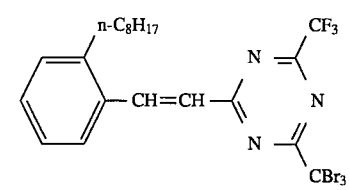
89.
90.

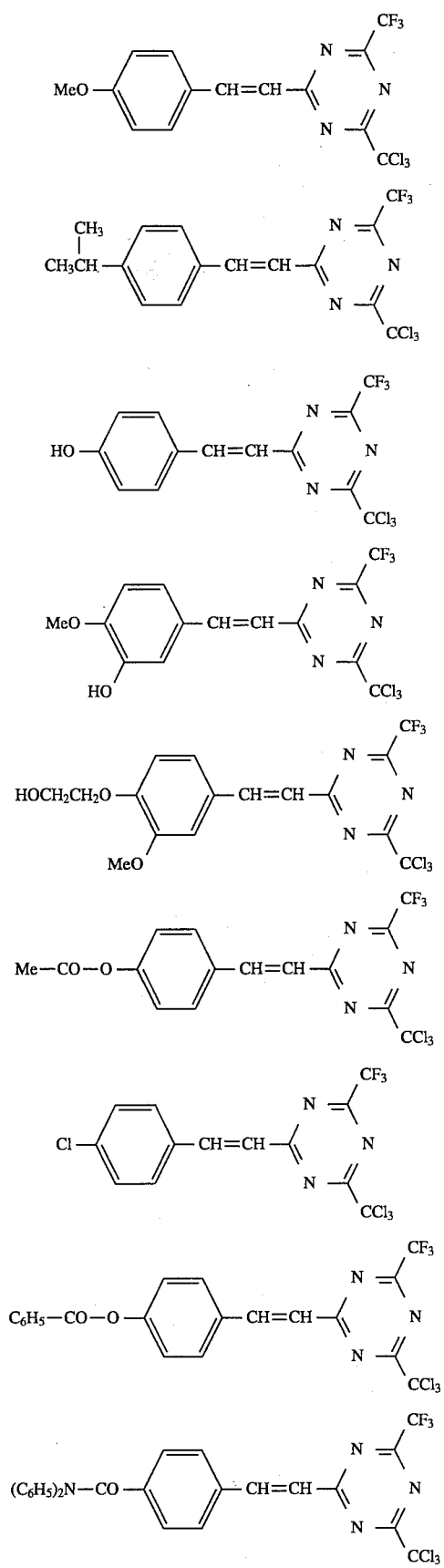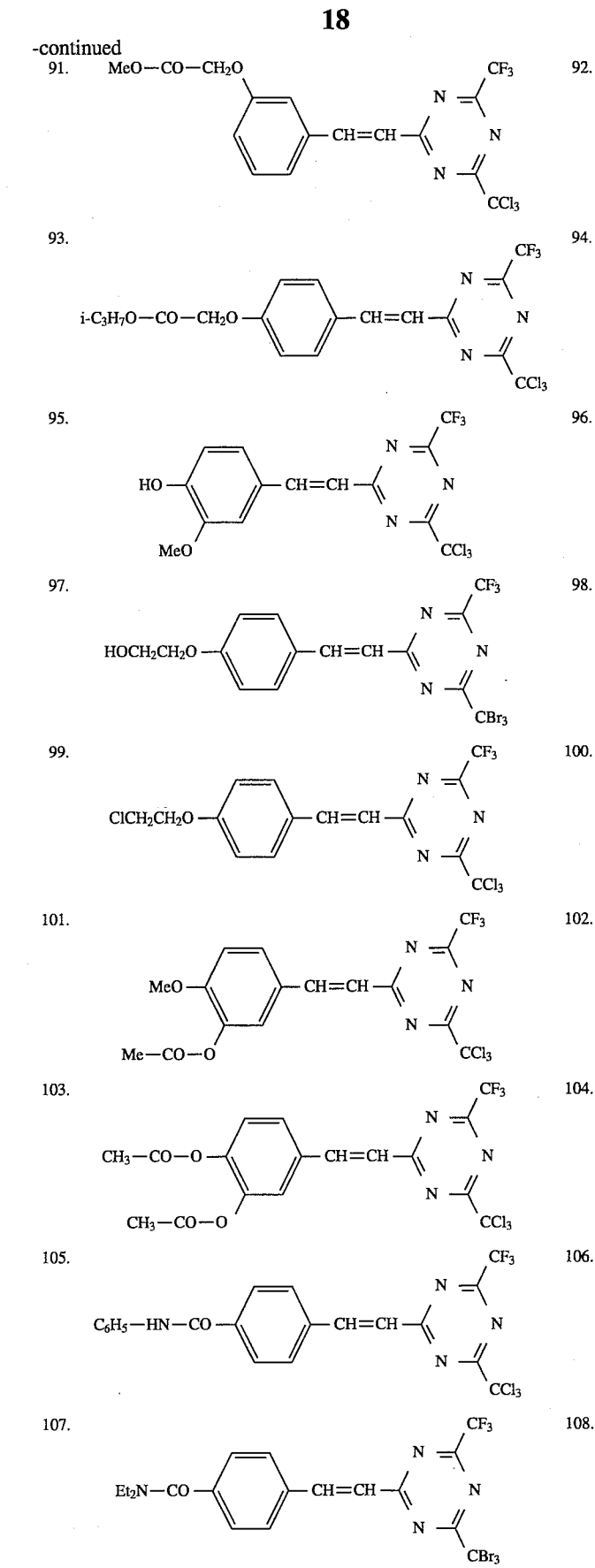

-continued
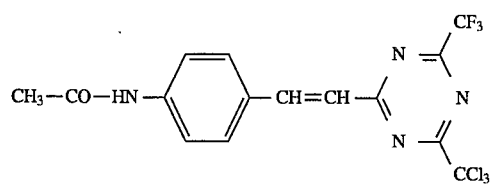 109.
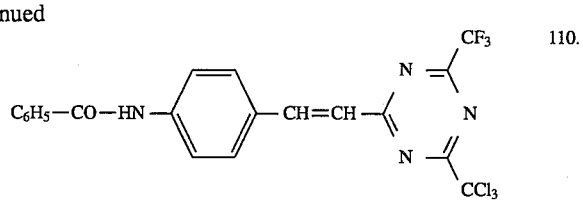 110.
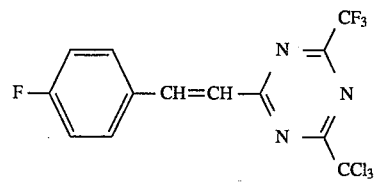 111.
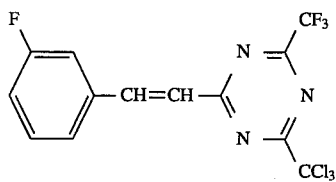 112.
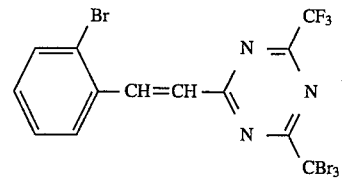 113.
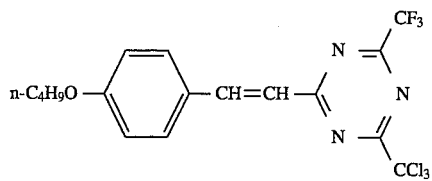 114.
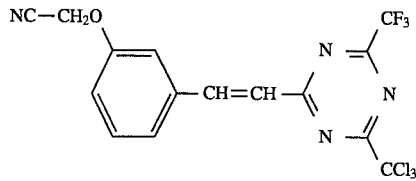 115.
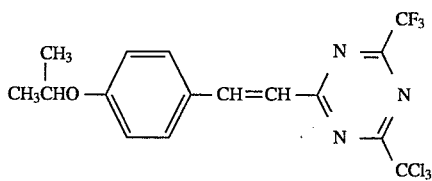 116.
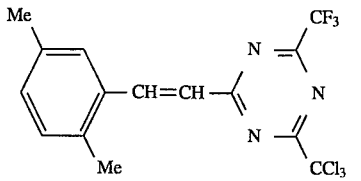 117.
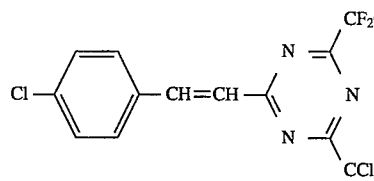 118.
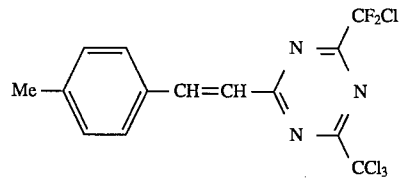 119.
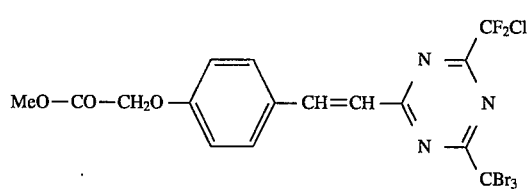 120.
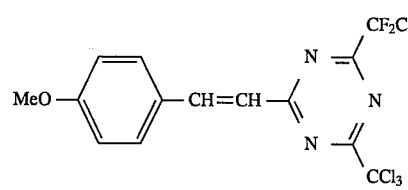 121.
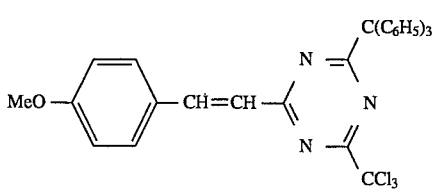 122.
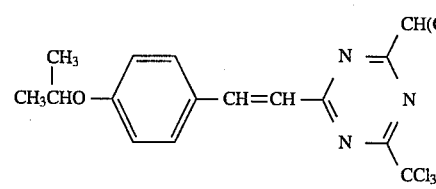 123.
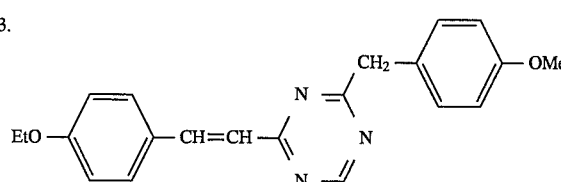 124.
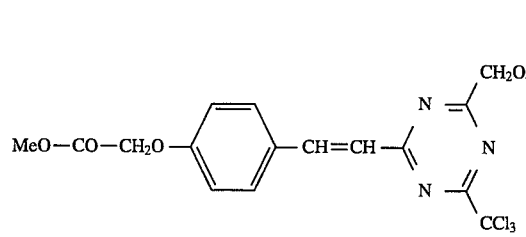 125.
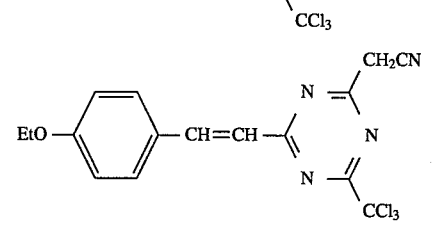 126.

-continued
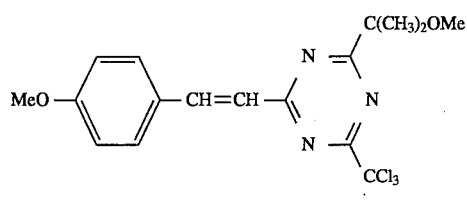 127.
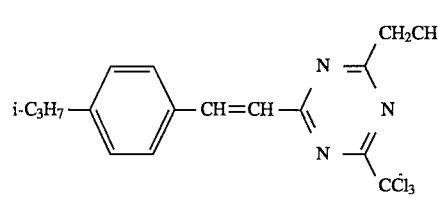 128.
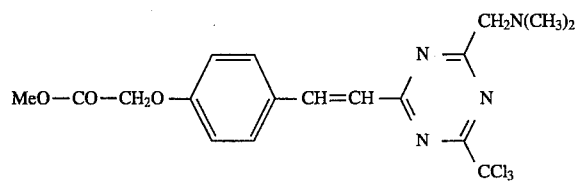 129.
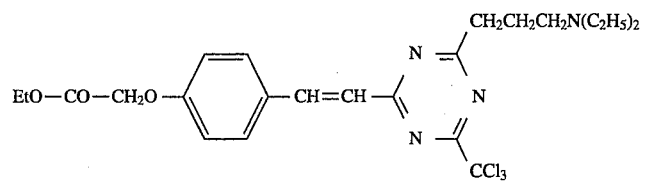 130.
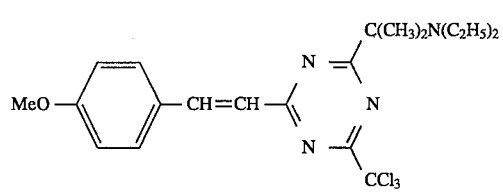 131.
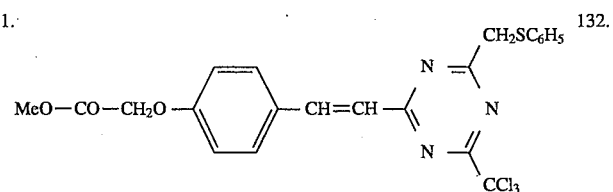 132.
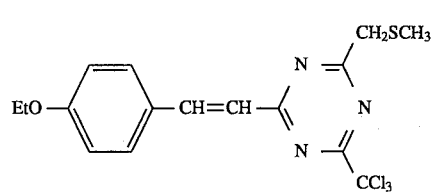 133.
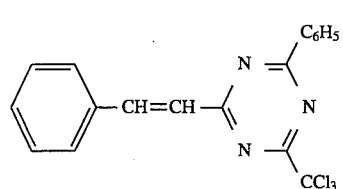 134.
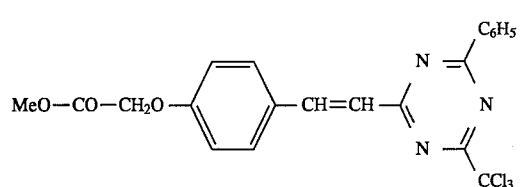 135.
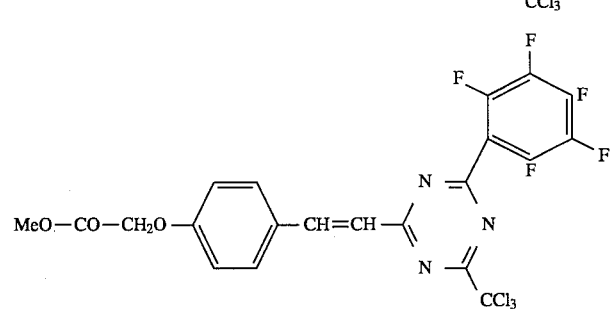 136.

-continued
137.
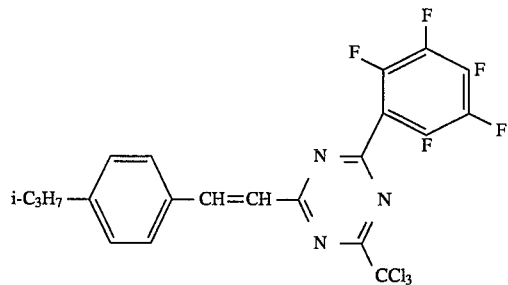
138.
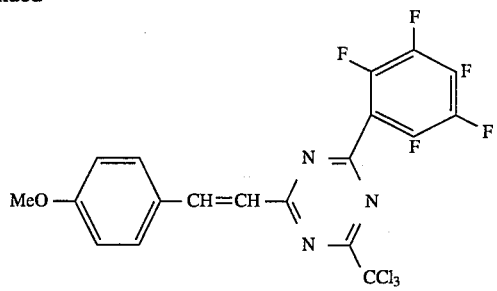
139.
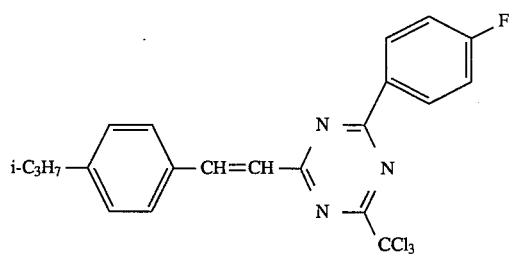
140.
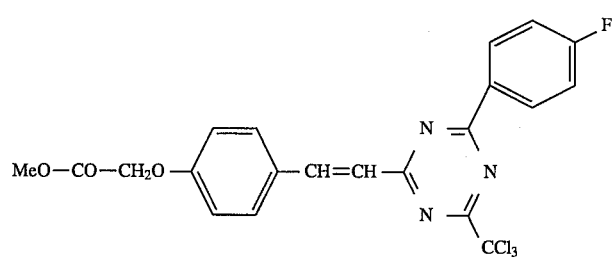
141.
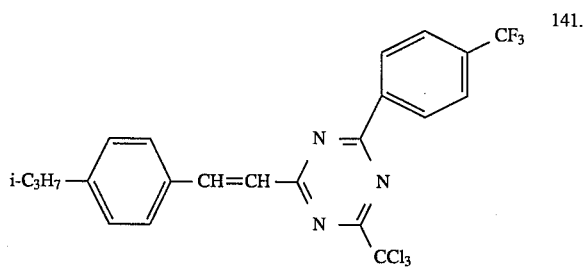
142.
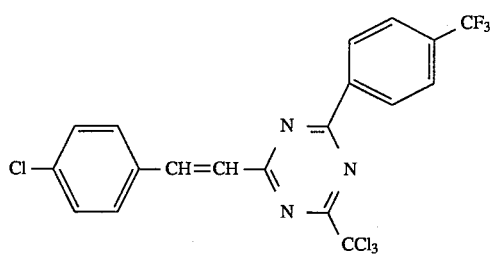
143.
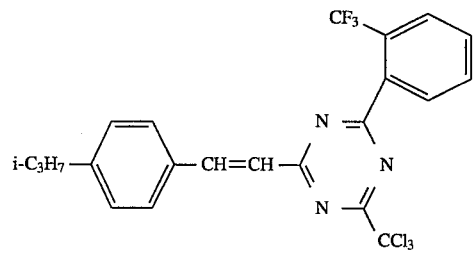
144.
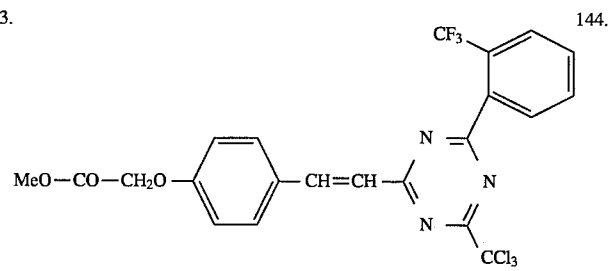
145.
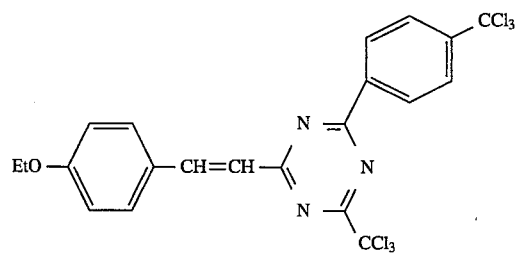

-continued
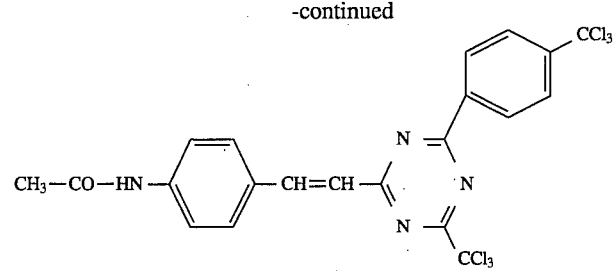
146.
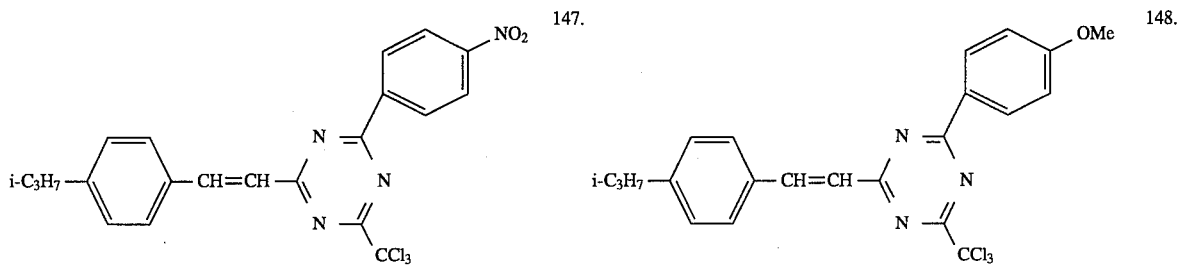
147.
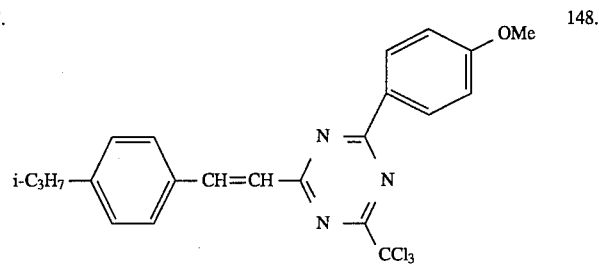
148.
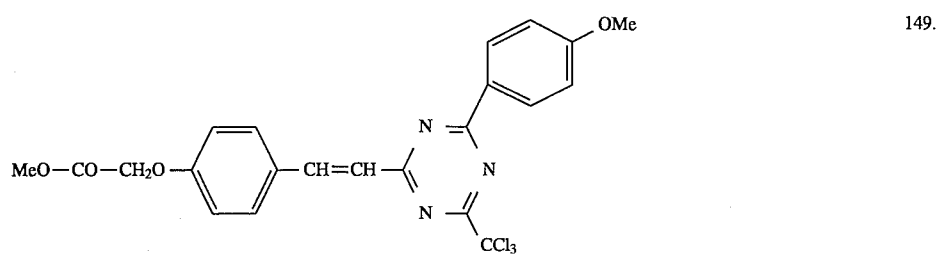
149.
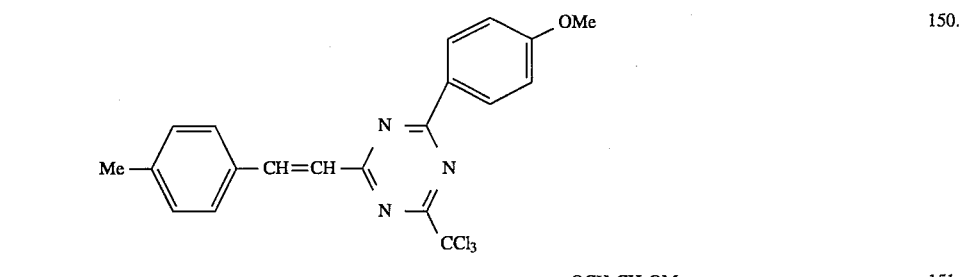
150.
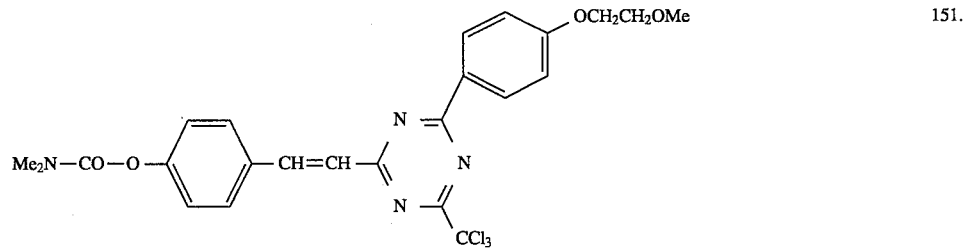
151.
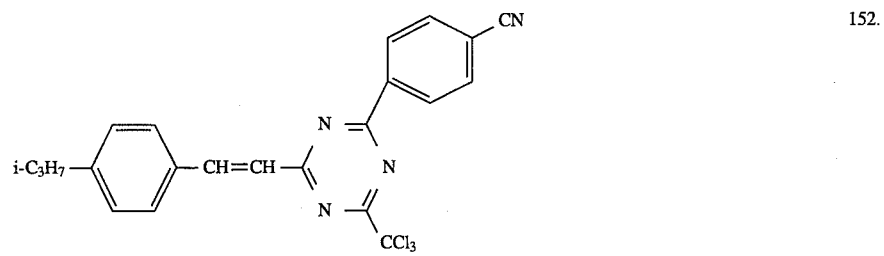
152.

-continued
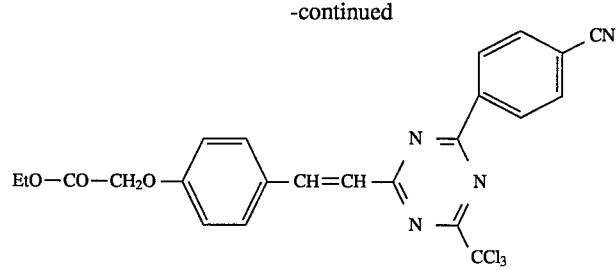
153.
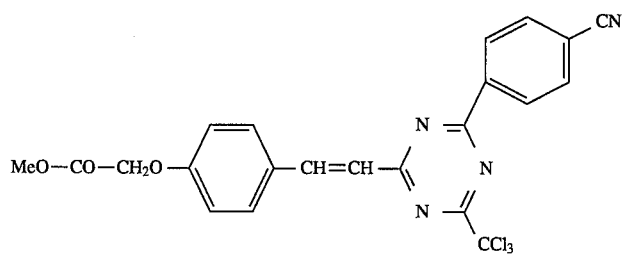
154.
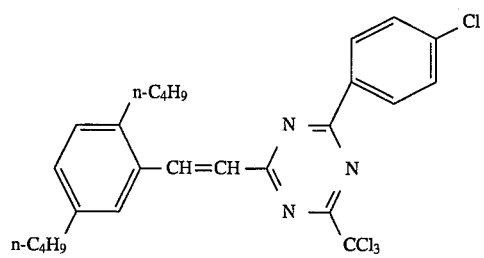
155.
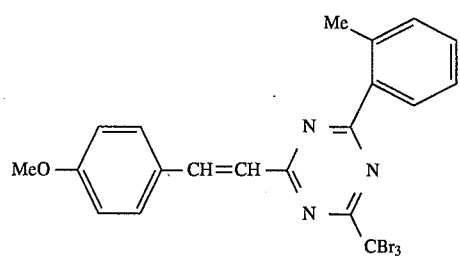
156.
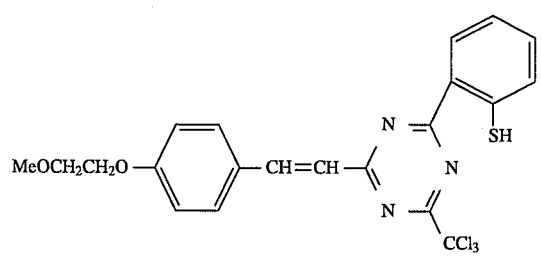
157.
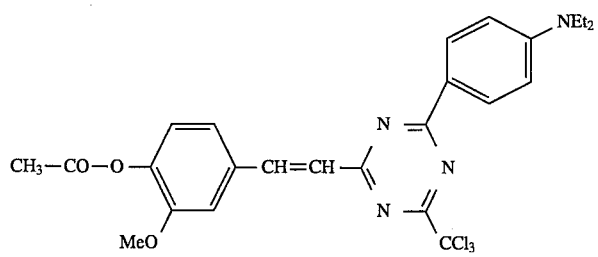
158.
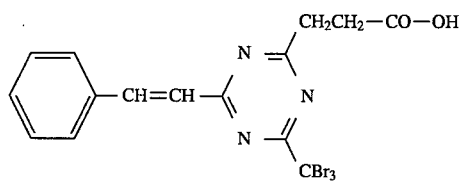
159.
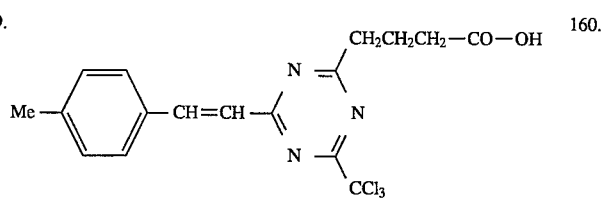
160.
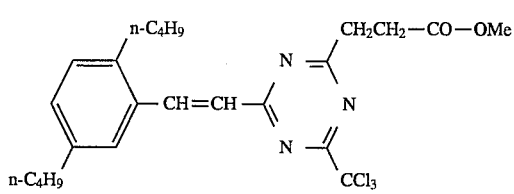
161.
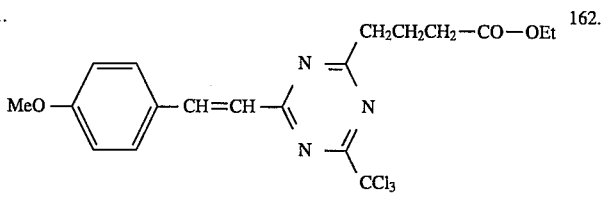
162.

-continued

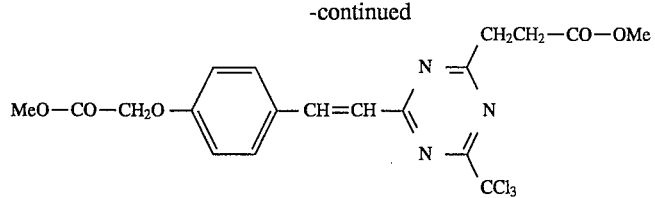

163.

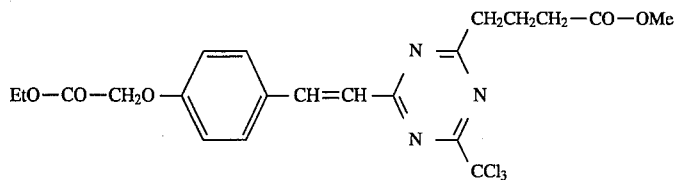

164.

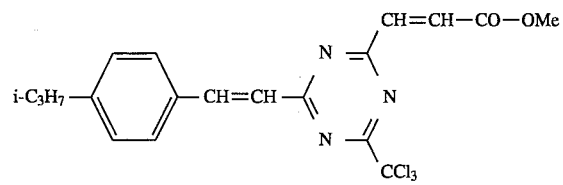

165.

The photosensitive trihalomethyl-s-triazine compound according to the present invention can be synthesized in accordance with the reaction scheme A or B:

Reaction Scheme A

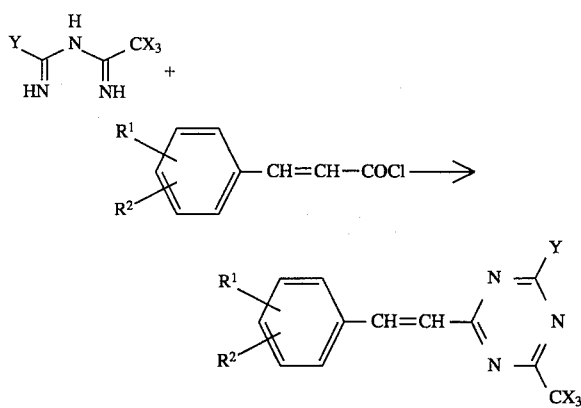

Reaction Scheme B

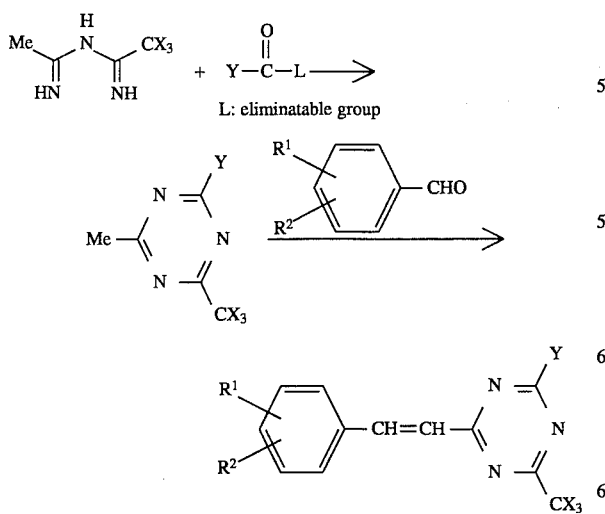

In the reaction scheme A, N-iminoacyltrihaloacetamidine and acid chloride are reacted with each other. In the reaction scheme B, N-(acetymidyl) trihaloacetamidine and a carboxylic acid derivative are reacted with each other to synthesize methyl-trihalomethyl-s-triazine which is then allowed to undergo a condensation reaction with a specific aldehyde or aldehyde derivative.

The synthesis of trihalomethyl-s-triazine in the reaction scheme A and the synthesis of methyl-trihalomethyl-s-triazine in the reaction scheme B can be easily accomplished by the method described in British Patent 912,112. The condensation reaction in the reaction scheme B can be accomplished by the method described in U.S. Pat. No. 3,987,037.

As the acid chloride to be reacted in the reaction scheme A there may be used one which is commercially available or has been synthesized from a carboxylic acid. As the aldehyde to be reacted in the reaction scheme B, one which is commercially available or has been synthesized by a known method can be used.

The compound of formula (I) wherein Y is —Z—CO—OR$^{12}$ (in which R$^{12}$ represents an alkyl group represented by R$^3$) can be also synthesized in accordance with the following reaction scheme C:

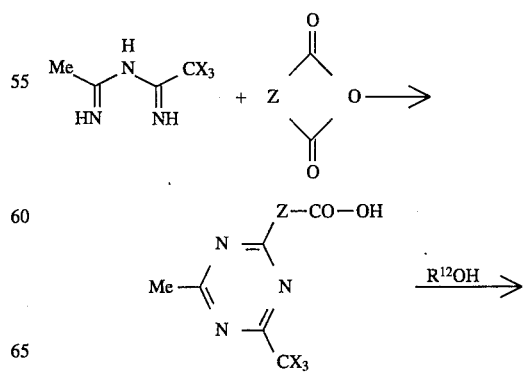

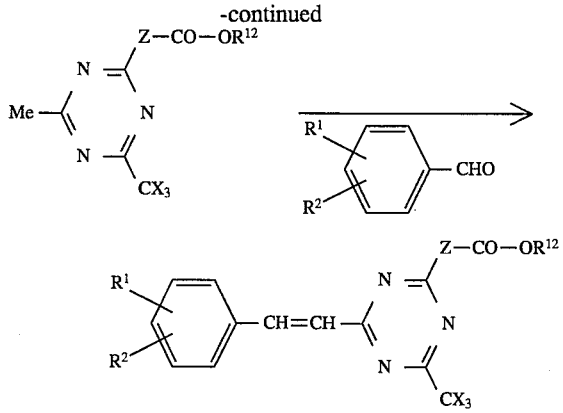

In the reaction scheme C,

N-(acetymidyl)triacetamidine is reacted with a cyclic acid anhydride. This method can synthesize a carboxyl-terminated s-triazine derivative. The resulting carboxyl group is then esterified by an ordinary method so that an alkoxycarbonyl group can be derived therefrom.

The photosensitive trihalomethyl-s-triazine compound represented by formula (I) is particularly useful as a radical photopolymerization initiator to be incorporated in a photopolymerizable composition.

A photopolymerizable composition comprising a photosensitive trihalomethyl-s-triazine compound represented by formula (I) incorporated therein normally comprises a polymerizable compound having ethylenically unsaturated bonds, a radical photopolymerization initiator, and optionally a binder, more optionally a sensitizer. Thus, the photosensitive trihalomethyl-s-triazine compound represented by formula (I) is particularly useful in a photosensitive layer, color proof, photoresist, etc. and for a photosensitive printing plate.

The photosensitive trihalomethyl-s-triazine compound represented by formula (I) also finds good application in recording materials comprising a photopolymerizable composition mentioned below. However, the present invention is not limited to these uses.

These recording materials include a photosensitive heat-sensitive recording material which forms a latent image in a photo-setting composition upon exposure to light and then allows components taking part in coloration or decoloration to migrate in the light-sensitive material in correspondence to the latent image to form a color image, in which system at least one of the components taking part in coloration or decoloration is contained in microcapsules and the photo-setting composition comprises an ethylenically unsaturated compound and a photosentivie trihalomethyl-s-triazine compound according to the present invention. In the photosensitive heat-sensitive recording material, the components taking part in coloration or decoloration preferably comprise an electron donative colorless dye and an electron-accepting compound.

The polymerizable compound having ethylenically unsaturated bonds in the photopolymerizable composition of the present invention is a compound having at least one ethylenically unsaturated bond in its chemical structure and can be used in a form of a monomer, a prepolymer (e.g., dimer, trimer, other oligomers), mixtures thereof and copolymers thereof. Specific examples of such a polymerizable compound include those disclosed in U.S. Pat. Nos. 2,760,863, 3,030,023, JP-B-35-5093 (The term "JP-B" as used herein means an "examined Japanese patent publication"), JP-B-35-14719, and JP-B-44-28727. Examples of the compound include acrylic acid, salts thereof, ester acrylates, methacrylic acid, salts thereof, ester methacrylates, acrylamide, methacrylamide, maleic anhydride, ester maleates, itaconic acid, ester itaconates, styrenes, vinylethers, vinylesters, and arylesters.

Particularly preferred among them is a compound having at least two terminal unsaturated groups such as an acrylic ester, a methacrylic ester and an itaconic ester of a polyvalent alcohol, an acrylic amide and a methacrylic amide of a polyvalent amine, and an acrylate- or methacrylate-terminated epoxy resin. Specific examples of the ester acrylates include ethylene glycol diacrylate, diethylene glycol diacrylate, triethylene glycol diacrylate, 1,3-butanediol diacrylate, tetramethylene glycol diacrylate, tetraethylene glycol diacrylate, propylene glycol diacrylate, trimethylolpropane triacrylate, trimethylolethane triacrylate, 1,4-cyclohexanediol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol hexaacrylate, sorbitol triacrylate, sorbitol tetraacrylate, sorbitol hexaacrylate, and polyester acrylate oligomer. Examples of the ester methacrylates include ethylene glycol dimethacrylate, triethylene glycol dimethacrylate, tetramethylene glycol dimethacrylate, trimethylolpropane trimethacrylate, trimethylolethane trimethacrylate, 1,3-butanediol dimethacrylate, pentaerythritol dimethacrylate, pentaerythritol trimethacrylate, pentaerythritol tetramethacrylate, dipentaerythritol dimethacrylate, sorbitol tetramethacrylate, and 1,2,4-butanetriol trimethacrylate. Examples of the ester itaconates include ethylene glycol diitaconate, propylene glycol diitaconate, 1,3-butanediol diitaconate, 1,4-butanediol diitaconate, tetramethylene glycol diitaconate, pentaerythritol diitaconate, and sorbitol tetraitaconate. Examples of the amide acrylates include methylenebis-acrylamide, 1,6-hexamethylenebis-acrylamide, and diethylenetriamine trisacrylamide. Examples of the amide methacrylates include methylenebismethacrylamide, 1,6-hexamethylenebis-methacrylamide, and xylylenebismethacrylamide.

Also, an electron-accepting compound having at least one polymerizable ethylene group is preferred. Specific examples of the electron-accepting compound include benzoic methacryloxyethylesters as disclosed in JP-A-63-173682, acryloxyethylesters which can be synthesized in the same method as described in JP-A-63-173682, esters of benzoic acid having a hydroxyl group with hydroxymethylstyrene as disclosed in JP-A-59-83693, JP-A-60-141587, and JP-A-62-99190, hydroxystyrenes as disclosed in European Patent 29,323, N-vinylimidazole complexes of halogenated zinc as disclosed in JP-A-62-167077, and JP-A-62-16708, color developer monomers as described in JP-A-63-317558, and compounds represented by formula (V):

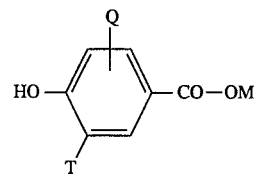

wherein T represents a hydrogen atom or a halogen atom; M represents a monovalent group having a polymerizable ethylene group; and Q represents a hydrogen atom, an alkyl group, a hydroxyl group, an acyloxy group or an alkoxy group. Preferred among the monovalent groups having a polymerizable ethylene group are vinyl-containing aralkyl, acryloyloxyalkyl and methacryolyloxyalkyl groups.

Specific examples of the monovalent group include vinylphenethylester 3-chloro-4-hydroxybenzoate, vinylphenylpropylester 3-chloro-4-hydroxybenzoate, 3-chloro-4-hydroxy-hydroxybenzoic acid-(2-acryloyloxyethyl)ester, 3-chloro-4-hydroxybenzoic acid-(2-methacryloyloxyethyl)ester, 3-chloro-4-hydroxybenzoic acid-(6-methacryloloxyhexyl)ester, 3-chloro-4-hydroxybenzoic acid-(6-acryloyloxyhexyl)ester, 3-chloro-4-hydroxybenzoic acid-(3-acryloyloxypropyl)ester, 3-chloro-4-hydroxybenzoic acid-(3-methacryloyloxypropyl)ester, 3-chloro-4-hydroxybenzoic acid-(4-acryloyloxybutyl)ester, 3-chloro-4-hydroxybenzoic acid-(4-methacryloyloxybutyl)ester, 3-fluoro-4-hydroxybenzoic acid-(2-acryloyloxyethyl)ester, vinylbenzylester 2,4-dihydroxy-6-methylbenzoate, vinylbenzylester 2,4-dihydroxy-5-methylbenzoate, vinylbenzylester 2,4-dihydroxy-3-methylbenzoate, vinylbenzylester 2,4-dihydroxy-3-chlorobenzoate, vinylbenzylester 2,4-dihydroxy-6-phenylbenzoate, vinylphenethylester 2,4-dihydroxybenzoate, vinylphenylpropylester 2,4-dihydroxybenzoate, vinylbenzylester 2,4-dihydroxybenzoate, 2-acryloyloxy- 4-hydroxybenzoic acid-(2-acryloyloxyethyl)ester, 2-methacryloyloxy-4-hydroxybenzoic acid-(2-methacryloyloxyethyl)ester, 2,4-dihydroxybenzoic acid-(2,3-bimethacryloyloxypropyl)ester, and 2,4-dihydroxybenzoic acid-(2,3-bisacryloyloxypropyl)ester.

The amount of the polymerizable compound having an ethylenically unsaturated bond is generally from 10 to 60% by weight, preferably from 25 to 50% by weight, based on the total solid content (components that remain in the solidified composition after photopolymerization) of the photopolymerizable composition of the present invention.

If the photosensitive trihalomethyl-s-triazine compound represented by formula (I) is used as a radical photopolymerization initiator to be incorporated in a photopolymerizable composition, the photopolymerizable composition may comprise a binder incorporated therein as necessary.

The binder to be incorporated in the photopolymerizable composition of the present invention needs to be compatible with the polymerizable ethylenically unsaturated compound and the radical photopolymerization initiator so that no demixing occurs during the preparation of the coating solution from the composition, all the procedures in the preparation of the photosensitive material between coating and drying, and the storage of the resulting mixture. Also, when incorporated in a photosensitive layer or resist layer to be developed with an alkaline aqueous solution, the binder needs to be capable of being subjected to development after imagewise exposure to light and forming a tough film as photosensitive layer, resist layer or protective layer. It may be properly selected from a variety of synthetic, semisynthetic and natural high molecular substances.

Specific examples of the binder which can be used in the present invention include copolymers of (meth)acrylic acid with (meth)acrylic ester (examples of the ester include methyl ester, ethyl ester, butyl ester, 2-ethylhexyl ester, benzyl ester, and 2-hydroxyethyl ester), poly(meth)acrylic acids, copolymers of styrene with unsaturated dibasic acid anhydride such as maleic anhydride, products of the reaction of the polymers with alcohols, products of the reaction of the polymers with polybasic acid anhydrides of cellulose, gelatin, and polyvinyl alcohols. However, the present invention should not be construed as being limited to these compounds. The term "(meth)acrylic" used herein means "acrylic or methacrylic".

These binders may be used singly. Two or more polymers which are quite compatible with each other and which do not cause demixing during the procedures in the preparation of the photosensitive material from the preparation of the coating solution through the coating of the coating solution to the drying of the coating and during the storage of the resulting mixture may be mixed in a proper proportion to provide a binder.

The molecular weight of the high molecular substances to be used as binder components can vary widely depending on the kind of polymer but is normally in the range of 5,000 to 2,000,000, preferably 10,000 to 1,000,000.

The amount of the binder is generally from 40 to 90% by weight, preferably from 50 to 70% by weight, based on the total solid content of the photopolymerizable composition of the present invention.

The photopolymerizable composition comprising the trihalomethyl-s-triazine derivative according to the present invention may also comprise a compound capable of initiating the photopolymerization of the other compound having an ethylenically unsaturated bond. Examples of such a photopolymerization initiator include organic sulfur compounds, peroxides, redox compounds, azo compounds, diazo compounds and substituted benzophenone derivatives as disclosed in J. Kosa (translator's note: This spelling is phonetic), "Light-sensitive Systems", Chapter 5, aromatic ketones, lophine dimers, and organic halogen compounds falling outside the present invention.

The amount of photopolymerization initiator to incorporate into the photopolymerizable composition is preferably in the range of 0.01 to 20% by weight, more preferably 0.2 to 15% by weight, most preferably 0.5 to 10% by weight based on the total weight of the photopolymerizable composition. If this value falls below 0.01% by weight, the resulting photosensitive material exhibits insufficient sensitivity. On the contrary, if this value exceeds 10% by weight, the resulting photosensitive material cannot be provided with a higher sensitivity. According to the present invention, the proportion of photosensitive trihalomethyl-s-triazine compound used in all the photopolymerization initiators is preferably not less than 40% by weight, more preferably not less than 50% by weight.

The photopolymerizable composition according to the present invention may further comprise a spectral sensitizing dye for adjusting the wavelength to which it is sensitive in addition to the ethylenically unsaturated compound and the trihalomethyl-s-triazine derivative. As such, various spectral sensitizing dye compounds known in the art may be used. For the details of these specific sensitizing dyes, reference can be made to the foregoing patents concerning photopolymerization initiator, Research Disclosure, Vol. 200, Dec. 1980, Item 20036, and Katsumi Tokumaru & Shin Oogawara, "Sensitizer", Kodansha, 1987, pp. 160–163.

The amount of the spectral sensitizing dye is generally from 0.01 to 40% by weight, preferably from 0.2 to 20% by weight, particularly preferably from 0.5 to 15% by weight, based on the total solid content of the photopolymerizable composition of the present invention.

The photopolymerizable composition according to the present invention may further comprise auxiliaries for accelerating the polymerization thereof, a reducing agent such as an oxygen remover, and a chain transfer agent for an active hydrogen donor or other compounds for accelerating the polymerization thereof according to a chain transfer reaction. Examples of the oxygen remover include phosphine, phosphonate, phosphite, stannous salt, and other compounds which can be easily oxidized by oxygen. Specific examples of such compounds include N-phenylglycine, trimethylbarbiturtic acid, N,N-dimethyl-2,6-diisopropylaniline, and N,N,N-2,4,6-pentamethylaniline. Further, thiols, thioketones, trihalomethyl compounds, lophine dimer compounds, iodonium salts, sulfonium salts, azinium salts and organic peroxides as mentioned below are useful as polymerization accelerators.

Besides these compounds, the photopolymerizable composition may further comprise vinyl polycinnamate, vinyl polycinnamylideneacetate, photosensitive resins having an α-phenylmaleimide group, etc. incorporated therein.

The photopolymerizable composition may further comprise a thermal polymerization inhibitor as necessary. The thermal polymerization inhibitor is adapted to inhibit the thermal polymerization of a photopolymerizable composition or the polymerization thereof with time. With such a thermal polymerization inhibitor, the chemical stability of the photopolymerizable composition during the preparation or storage thereof can be enhanced.

The photopolymerizable composition of the present invention may comprise various surface active agents incorporated therein for the purpose of assisting coating and emulsion dispersion, inhibiting electrification and adhesion, improving smoothness, or like purposes.

As the surface active agent there may be used a nonionic surface active agent such as saponin, polyethylene oxide, polyethylene oxide derivative (e.g., alkylether of polyethylene oxide), an anionic surface active agent such as alkylsulfonate, alkylbenzenesulfonate, alkylnaphthalenesulfonate, ester alkylsulfate, N-acyl-N-alkyltaurines, ester sulfosuccinates and sulfoalkyl polyoxyethylene alkylphenylethers, amphoteric surface active agents such as alkylbetaines and alkylsulfobetaines, or cationic surface active agents such as aliphatic or aromatic quaternary ammoniums as necessary.

The photopolymerizable composition of the present invention may comprise a plasticizer incorporated therein to control the physical properties of the film. Examples of the plasticizer include ester phthalates such as diethyl phthalate, dibutyl phthalate and dioctyl phthalate, glycol esters such as triethyleneglycoldicaprylate, ester phosphates such as tricresyl phosphate, aliphatic dibasic esters such as dioctyl adipate and dibutyl sebacate, and amides such as benzenesulfonamide and toluenesulfonamide.

The photopolymerizable composition of the present invention may comprise an adhesion accelerator to enhance the adhesion thereof.. Examples of the adhesion accelerator include compounds as described in JP-B-50-9177 (The term "JP-B" as used herein means an "examined Japanese patent publication"), JP-B-54-5292, JP-B-55-22481, JP-B-57-49894, and U.S. Pat. No. 4,629,679.

The recording material of the present invention may comprise various additives, including those described above, incorporated therein as necessary. Typical examples of anti-irradiation or anti-halation dyes, leuco dyes, ultraviolet absorbents, fluorescent brightening agents, matting agents, coating aids, hardeners, anti-static agents and slipperiness improvers are described in Research Disclosure, Vol. 176, Dec. 1978, Item 17643, and Vol. 187, Nov. 1979, Item 18716.

The photopolymerizable composition of the present invention may be dissolved or dispersed in a solvent or dispersed in water to prepare a coating solution which is then applied to a support by a proper method. The resulting coating can be used as an image-forming material. It may be topcoated by a protective layer or protective film.

As the solvent for use in the preparation of the coating solution there may be used natural oil or synthetic oil as well. Examples of the solvent include cottonseed oil, kerosine, paraffin, naphthenic oil, alkylated biphenyl, alkylated terphenyl, chlorinated paraffin, alkylated naphthalene, diarylethane such as 1-phenyl-1-xylylethane, 1-phenyl-1-p-ethylphenylethane and 1,1'-ditolylethane, ester phthalate, ester phosphate, ester citrate, ester benzoate, alkylamide, aliphatic esters, trimesic esters, secondary butyl alcohol, methyl isobutyl ketone, β-ethoxyethyl acetate, methylcellosolve acetate, 1-methoxy-2-propyl acetate, cyclohexanone, ethanol, propanol, acetone, methyl ethyl ketone, toluene, xylene, methyl chloroform, chlorinated methylene, ethylene glycol monoethyl ether, 1-methoxy- 2-propanol, dimethylformamide, and dimethylsulfoxide.

The application of the coating solution to the support can be effected by means of a blade coater, rod coater, knife coater, roll doctor coater, comma coater, reverse roll coater, transfer roll coater, gravure coater, kiss-roll coater, curtain coater, extrusion coater or the like. For the method of applying the coating solution to the support, reference can be made to Research Disclosure, Vol. 200, Dec. 1980, Item 20036. The thickness of the recording layer is preferably in the range of 1.0 μm to 100 μm.

Examples of the support include a support material such as paper, coated paper, laminated paper and synthetic paper, transparent film such as polyethylene terephthalate film, cellulose triacetate film, polyethylene film, polystyrene film and polycarbonate film, plate of metal such as aluminum, zinc and copper, and support materials obtained by subjecting the foregoing support materials to various treatments such as surface treatment, undercoating and vacuum metallizing. For the details of the support, reference can be made to Research Disclosure, Vol. 200, Dec. 1980, Item 20036. These supports may optionally comprise an antihalation layer on one side thereof and a slip layer, antistatic layer, anticurling layer, adhesive layer or the like on the other side thereof depending on the purpose.

If the present invention is used as a resist for the preparation of printed wiring, a support obtained by vacuum-metallizing or plating a plastic plate or plastic film thinly with a metal such as copper. If the present invention is used as a printing plate, an aluminum plate, a plastic film provided with an aluminum layer or the like may be used. If the present invention is used as a photosensitive heat-sensitive recording material, paper, coated paper, laminated paper, synthetic paper, or transparent film such as polyethylene terepthalate film, cellulose triacetate film, polyethylene film, polystyrene film and polycarbonate film may be used.

When used in recording, the recording material of the present invention thus obtained is highly sensitive to light of a wavelength ranging from ultraviolet region to visible light range. A variety of light sources such as a mercury vapor lamp, a xenon lamp, a tungsten lamp, a metal halide lamp, various lasers (e.g., an argon laser, a helium neon laser and a semiconductor laser), an LED and a fluorescent tube may be used.

The wavelength range of light within which the photopolymerizable composition of the present invention has high sensitivity is generally about from 300 to 800 nm, preferably from 320 to 500 nm.

The recording of an image can be effected by various exposure methods such as contact exposure of an original such as a lith film, enlarged exposure using a slide or liquid crystal and reflective exposure using reflected light from an original. The recording material which has thus been imagewise exposed to light is then processed with a proper developer such as an organic solvent, an alkaline aqueous solution containing an organic solvent and an alkaline aqueous solution to elute the unexposed area away. Thus, a photo-cured image is formed on the support. In the case of a photosensitive heat-sensitive recording material, it is directly subjected to heat development to obtain an image. The photopolymerizable composition of the present invention finds wide application in the preparation of resist for printed wiring, lithographing printing plate or letterpress, relief form, photosensitive heat-sensitive recording material, etc.

The present invention will be further described in the following examples, but the present invention should not be construed as being limited thereto. Unless otherwise indicated, all parts, percents, ratios and the like are by weight.

EXAMPLE I

Synthesis of Compound 7

Compound 7

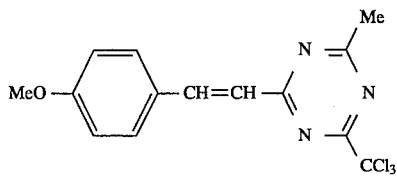

A. Synthesis by the Reaction Scheme A 2.8 g of N-(acetymidyl)trichloroacetamidine, 4.7 g of p-methoxycinnamic chloride and 60 ml of benzene were mixed. The mixture was then heated under reflux for 8 hours. The reaction solution was then extracted with ethyl acetate. The ethyl acetate solution thus extracted was washed with water, and then distilled off under reduced pressure. The resulting residue was purified through column chromatography, and then recrystallized from methanol to obtain 0.59 g of Compound 7 in the form of a light yellow needle crystal having a melting point of 138° C.

¹HNMR(CDCl₃) δ(TMS, ppm) 8.33 (1H, d), 7.64 (2H, d), 7.06 (1H, d), 6.96 (2H, d), 3.87 (3H, s), 2.89 (3H, s).

UV spectrum (CH₃CN) $\lambda_{max}$351 nm (ε34800).

B. Synthesis by the Reaction Scheme B 4.1 g of N-(acetymidyl)trichloroacetamidine and 20 ml of acetic anhydride were mixed. The mixture was then heated under reflux for 1.5 hours. The internal temperature of the reaction system was allowed to cool to room temperature. The reaction solution was then poured into ice-water. The resulting solid was recovered by filtration to obtain 3.3 g of 2,4-dimethyl-6-trichloromethyl-s-triazine.

3.3 g of 2,4-dimethyl-6-trichloromethyl-s-triazine thus obtained, 2.2 g of p-anisaldehyde, 1.0 g of piperidine acetate and 15 ml of toluene were mixed. The mixture was heated under reflux for 20 hours while water released was being recovered by Dean-Stark's extractor. The reaction solution was then extracted with ethyl acetate. The ethyl acetate solution thus extracted was washed with water, and then distilled off under reduced pressure. The resulting residue was purified through column chromatography, and then recrystallized from methanol to obtain 1.4 g of Compound 7 in the form of a light yellow needle crystal having a melting point of 138° C.

EXAMPLE 2

Synthesis of Compound 1

Compound 1

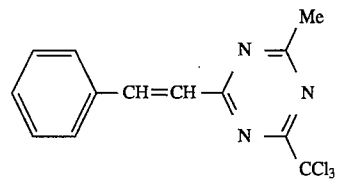

4.8 g of 2,4-dimethyl-6-trichloromethyl-s-triazine, 3.2 g of benaldehyde, 1.3 g of piperidine acetate and 20 ml of toluene were mixed. The mixture was heated under reflux for 10 hours while water released was being recovered by Dean-Stark's extractor. The reaction solution was then extracted with ethyl acetate. The ethyl acetate solution thus extracted was washed with water, and then distilled off under reduced pressure. The resulting residue was purified through column chromatography, and then recrystallized from methanol to obtain 0.4 g of Compound 1 in the form of a white crystal having a melting point of 80° C.

¹HNMR (CDCl₃) δ(TMS, ppm) 8.35 (1H, d), 7.70–7.65 (2H, m), 7.46–7.40 (3H, m), 7.20 (1H, d), 2.80 (3H, s).

UV spectrum (CH₃CN) $\lambda_{max}$318 nm (ε27200).

EXAMPLE 3

Synthesis of Compound 2

Compound 2

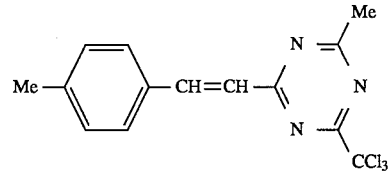

The same operation was conducted as in Example 2 except that 3.2 g of benzaldehyde was replaced by 4.1 g of tolualdehyde. 1.7 g of Compound 2 was obtained in the form of a white crystal having a melting point of 117° C.

¹HNMR(CDCl₃) δ(TMS, ppm) 8.33 (1H, d), 7.59 (2H, d), 7.24 (2H, d), 7.15 (1H, d), 2.80 (3H, s), 2.40 (3H, s).

UV spectrum (CH₃CN) $\lambda_{max}$331 nm (ε33100).

EXAMPLES 4 THROUGH 7

Compounds 13, 9, 3 and 5 were obtained in the same manner as in Example 2.

The physical properties of the compounds thus obtained are set forth below.

Compound 13

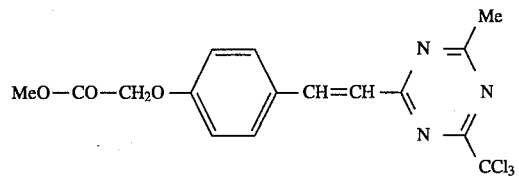

Melting point: 112–113° C. ¹HNMR(CDCl₃) δ(TMS, ppm) 8.20 (1H, d), 7.63 (2H, d), 7.07 (1H, d), 6.96 (2H, d), 4.70 (2H, s), 3.82 (3H, s), 2.80 (3H, s).

UV spectrum (CH₃CN) $\lambda_{max}$345 nm (ε31900).

Compound 9

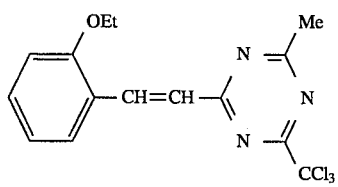

Melting point: 115°–117° C. ¹HNMR (CDCl₃) δ(TMS, ppm ) 8.73 (1H, d), 7.73–7.66 (1H, m), 7.42–7.24 (2H, 7.05–6.95 (1H, m), 6.94 (1H, d), 4.19 (2H, q), 2.80 (3H, s), 1.55 (3H, t).

UV spectrum (CH₃CN) $\lambda_{max}$355 nm (ε19300).

Compound 3

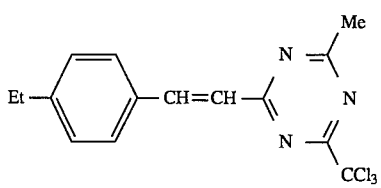

Melting point: 50°–52° C. ¹HNMR (CDCl₃) δ(TMS, ppm ) 8.33 (1H, d), 7.60 (2H, d), 7.27 (2H, d), 7.15 (1H, d), 2.80 (3H, s), 2.70 (2H, q), 1.28 (3H, t).

UV spectrum (CH₃CN) $\lambda_{max}$332 nm (ε29000)

Compound 5

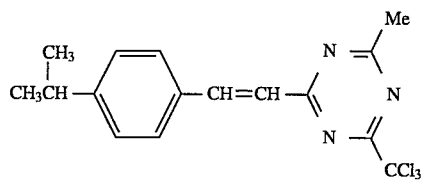

Melting point: 72°–74° C. ¹HNMR (CDCl₃) δ(TMS, ppm ) 8.33 (1H, d), 7.62 (2H, 7.30 (2H, d), 7.15 (1H, 2.96 (1H, dq), 2.79 (3H, s), 1.30 (6H, d).

UV spectrum (CH₃CN) $\lambda_{max}$331 nm (ε29500).

EXAMPLE 8

Synthesis of Compound 61

Compound 61

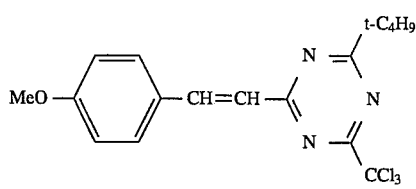

4.1 g of N-(acetymidyl)trichloroacetamidine and 20 ml of propionic anhydride were mixed. The mixture was then heated under reflux for 2 hours. The internal temperature of the reaction system was allowed to cool to room temperature. The reaction solution was then extracted with ethyl acetate. The ethyl acetate solution thus extracted was washed with water, and then distilled off under reduced pressure. The resulting residue was then purified through column chromatography to obtain 3.6 g of 2-methyl-4-ethyl-6-trichloromethyl-s-triazine.

3.6 g of 2-methyl-4-ethyl-6-trichloromethyl-s-triazine thus obtained, 2.2 g of p-anisaldehyde, 1.0 g of piperidine acetate and 15 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography, and then recrystallized from methanol to obtain 0.3 g of Compound 61 in the form of a light yellow crystal having a melting point of 92° C.

¹HNMR(CDCl₃) δ(TMS, ppm) 8.72 (1H, d ), 7.73–7.67 (1H, m), 7.42–7.24 (2H, m), 7.05–6.92 (2H, m), 4.18 (2H, q), 2.80 (3H, s), 1.55 (3H, t).

UV spectrum (CH₃CN) $\lambda_{max}$350 nm (ε30000).

EXAMPLE 9

Synthesis of Compound 91

Compound 91

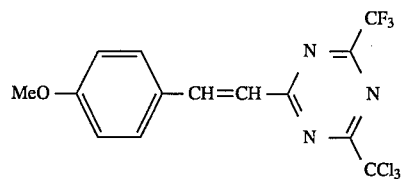

4.1 g of N-(acetymidyl)trichloroacetamidine and 20 ml of trifluoroacetic anhydride were mixed. The mixture was then heated under reflux for 2 hours. The internal temperature of the reaction system was allowed to cool to room temperature. The reaction solution was then extracted with ethyl acetate. The ethyl acetate solution thus extracted was washed with water, and then distilled off under reduced pressure to obtain 4.0 g of 2-methyl- 4-trichloromethyl-6-trifluoromethyl-s-triazine.

4.0 g of 2-methyl-4-trichloromethyl- 6-trifluoromethyl-s-triazine thus obtained, 2.2 g of p-anisaldehyde, 1.0 g of piperidine acetate and 15 ml of toluene were mixed. The mixture was heated under reflux for hours while water released was being recovered by Dean-Stark's extractor. The reaction solution was then extracted with ethyl acetate. The ethyl acetate solution thus extracted was washed with water, and then distilled off under reduced pressure. The resulting residue was purified through column chromatography, and then recrystallized from methanol to obtain 1.1 g of Compound 91 in the form of a light yellow crystal having a melting point of 125° C.

¹HNMR(CDCl₃) δ(TMS, ppm) 8.47 (1H, d), 7.70 (2H, d), 7.17 (1H, d), 6.99 (2H, d), 3.90 (3H, s).

UV spectrum (CH₃CN) $\lambda_{max}$374 nm (ε33800).

EXAMPLE 10

Synthesis of Compound 93

Compound 93

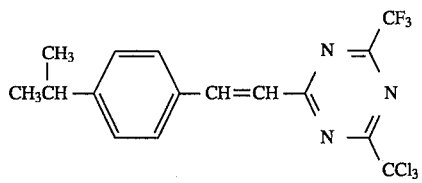

The same operation was conducted as in Example 9 except that 2.2 g of p-anisaldehyde was replaced by 4.4 g of cuminaldehyde. 0.2 g of Compound 93 was obtained in the form of a white crystal having a melting point of 77° to 79° C.

$^1$HNMR (CDCl$_3$) δ(TMS, ppm ) 8.48 (1H, d), 7.66 (2H, d), 7.34 (2H, d), 7.22 (1H, d), 2.98 (1H, dq), 1.30 (6H, d).

UV spectrum (CH$_3$CN) $\lambda_{max}$350 nm (ε32600).

EXAMPLE 11

Synthesis of Compound 103

Compound 103

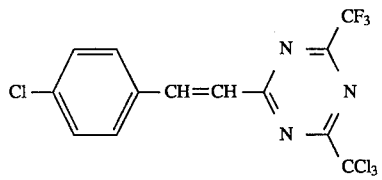

The same operation was conducted as in Example 9 except that 2.2 g of p-anisaldehyde was replaced by 4.2 g of p-chlorobenzaldehyde. 0.3 g of Compound 103 was obtained in the form of a white crystal having a melting point of 118° to 119° C.

$^1$HNMR(CDCl$_3$) δ(TMS, ppm) 8.45 (1H, d), 7.77 (2H, d), 7.46 (2H, d), 7.20 (1H, d), UV spectrum (CH$_3$CN) $\lambda_{max}$338 nm (ε34600).

EXAMPLE 12

Synthesis of Compound 88

2.8 g of 2-methyl-4-fluoromethyl-6-trichloromethyl-s-triazine, 1.8 g of tolualdehyde, and 1.5 g of ammonium acetate were mixed, and the mixture was then heated under reflux for 10 hours. The reaction solution was extracted with ethyl acetate. The ethyl acetate solution thus extracted was washed with water, and then distilled off under reduced pressure. The resulting residue was then purified through column chromatography and then recrystalized from methanol to obtain 1.6 g of Compound 88 in the form of a white crystal having a melting point of 108° C.

$^1$HNMR (CDCl$_3$) δ(TMS, ppm ) 8.48 (1H, d), 7.62 (2H, d), 7.29 (2H, d), 7.27 (1H, d), 2.43 (3H, s).

UV spectrum (CH$_3$CN) $\lambda_{max}$349 nm (ε25700).

EXAMPLE 13

Synthesis of Compound 95

The same operation was conducted as in Example 12 except that 1.8 g of tolualdehyde was replaced by 1.8 g of p-hydroxybenzaldehyde. 1.8 g of Compound 95 was obtained in the form of a yellow crystal having a melting point of 165°–167° C.

$^1$HNMR (CDCl$_3$) δ(TMS, ppm ) 8.45 (1H, d), 7.67 (2H, d), 7.24–7.10 (2H, m), 6.93 (2H, d), 5.17 (1H, brs).

UV spectrum (CH$_3$CN) $\lambda_{max}$375 nm (ε30600).

EXAMPLE 14

Synthesis of Compound 96

The same operation was conducted as in Example 12 except that 1.8 g of tolualdehyde was replaced by 2.0 g of vanillin. 1.0 g of Compound 96 was obtained in the form of a yellow crystal having a melting point of 161° C.

$^1$HNMR(CDCl$_3$) δ(TMS, ppm) 8.40 (1H, d), 7.32–7.10 (3H, m), 6.98 (1H, d), 6.05 (1H, brs), 3.98 (3H, s).

UV spectrum (CH$_3$CN) $\lambda_{max}$390 nm (ε30500).

EXAMPLE 15

Synthesis of Compound 119

20.3 g of N-(acetymidyl)trichloroacetamidine, 15.0 g of chlorodifluoroacetylchloride, and 200 ml of toluene were mixed at 0° C. 13.9 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure. The resulting residue was then purified through column chromatography to obtain 7.7 g of 2-methyl- 4-chlorodifluoromethyl-6-trichloromethyl-s-triazine.

3.0 g of 2-methyl-4-chlorodifluoromethyl- 6-trichloromethyl-s-triazine thus obtained, 1.3 g of tolualdehyde, 0.8 g of ammonium acetate, and 10 ml of acetonitrile were mixed. The mixture was heated under reflux for 10 hours. The reaction solution was then extracted with ethyl acetate. The ethyl acetate solution thus extracted was washed with water, and then distilled off under reduced pressure. The resulting residue was recrystallized from methanol to obtain 1.4 g of Compound 119 in the form of a light yellow crystal having a melting point of 120°–122° C.

$^1$HNMR (CDCl$_3$) δ(TMS, ppm ) 8.47 (1H, d), 7.63 (2H, d), 7.29 (2H, d), 7.25 (1H, d), 2.43 (3H, s).

UV spectrum (CH$_3$CN) $\lambda_{max}$349 nm (ε32000).

EXAMPLE 16

Synthesis of Compound 118

The same operation was conducted as in Example 15 except that 1.3 g of tolualdehyde was replaced by 1.6 g of p-chlorobenzaldehyde. 0.9 g of Compound 118 was obtained in the form of a white crystal having a melting point of 155° C.

$^1$HNMR (CDCl$_3$) δ(TMS, ppm) 8.45 (1H, d), 7.67 (2H, d), 7.45 (2H, d), 7.30 (1H, d).

UV spectrum (CH$_3$CN) $\lambda_{max}$338 nm (ε32000)

EXAMPLE 17

Synthesis of Compound 61

10.2 g of N-(acetymidyl)trichloroacetamidine, 6.2 ml of pivaloylchloride, and 100 m[of toluene were mixed at 0° C. 7 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure to obtain 10.5 g of 2-methyl-4-t-butyl-6-trichloromethyl-s-triazine.

2.8 g of 2-methyl-4-t-butyl-6-trichloromethyl-s-triazine thus obtained, 1.5 g of p-anisaldehyde, 1.4 g of piperidine acetate, and 10 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 0.33 g of Compound 61 in the form of a light yellow crystal having a melting point of 93°–94° C.

$^1$HNMR (CDCl$_3$) δ(TMS, ppm) 8.30 (1H, d), 7.65 (2H, d), 7.10 (1H, d), 6.96 (2H, d), 3.89 (3H, s), 1.48 (9H, s).

UV spectrum (CH$_3$CN) $\lambda_{max}$349 nm (ε35000).

EXAMPLE 18

Synthesis of Compound 62

The same operation was conducted as in Example 17 except that 1.5 g of p-anisaldehyde was replaced by 2.1 g of p-methoxycarbonylmethoxybenzaldehyde. 1.0 g of Compound 62 was obtained in the form of a white crystal having a melting point of 92° C.

$^1$HNMR (CDCl$_3$) δ(TMS, ppm ) 8.3o (1H, d), 7.65 (2H, d), 7.10 (1H, d), 6.95 (2H, d), 4.70 (2H, s), 3.83 (3H, s), 1.48 (9H, s).

UV spectrum (CH$_3$CN) $\lambda_{max}$340 nm (ε25500).

EXAMPLE 19

Synthesis of Compound 60

The same operation was conducted as in Example 17 except that 1.5 g of p-anisaldehyde was replaced by 1.3 g of tolualdehyde. 0.8 g of Compound 60 was obtained in the form of a white crystal having a melting point of 95° C.

$^1$HNMR(CDCl$_3$) δ(TMS, ppm ) 8.31 (1H, d), 7.59 (2H, d), 7.25 (2H, d), 7.20 (1H, d), 2.40 (3H, s), 1.47 (9H, s).

UV spectrum (CH$_3$CN) $\lambda_{max}$328 nm (ε32400).

EXAMPLE 20

Synthesis of Compound 71

20.3 g of N-(acetymidyl)trichloroacetamidine, 13.9 ml of t-butylacetylchloride, and 200 ml of benzene were mixed at 0° C. 13.9 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure to obtain 9.6 g of 2-methyl-4-neopentyl-6-trichloromethyl-s-triazine in the form of a colorless liquid.

2.8 g of 2-methyl-4-neopentyl-6-trichloromethyl-s-triazine thus obtained, 1.5 g of p-anisaldehyde, 1.5 g of piperidine acetate, and 10 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 0.7 g of Compound 71 in the form of a light yellow crystal having a melting point of 100°–101° C.

$^1$HNMR (CDCl$_3$) δ(TMS, ppm) 8.30 (1H, d), 7.65 (2H, d), 7.09 (1H, d), 6.96 (2H, d), 3.87 (3H, s), 2.90 (2H, s), 1.08 (9H, s).

UV spectrum (CH$_3$CN) $\lambda_{max}$350 nm (ε30300).

EXAMPLE 21

Synthesis of Compound 70

The same operation was conducted as in Example 20 except that 1.5 g of p-anisaldehyde was replaced by 2.2 g of p-methoxycarbonylmethoxybenzaldehyde. 0.4 g of Compound 70 was obtained in the form of a white crystal having a melting point of 114° C.

$^1$HNMR(CDCl$_3$) δ(TMS, ppm ) 8.30 (1H, d), 7.65 (2H, d), 7.10 (2H, d), 6.96 (2H, d), 4.71 (2H, s), 3.84 (3H, s), 2.91 (2H, s), 1.09 (9H, s).

UV spectrum (CH$_3$CN) $\lambda_{max}$345 nm (ε29400).

EXAMPLE 22

Synthesis of Compound 75

20.3 g of N-(acetymidyl)trichloroacetamidine, 19.9 g of 1-adamantanecarbonylchloride, and 200 ml of benzene were mixed at 0° C. 13.9 ml of trimethylamine was added to the mixture, and then the mixture was heated under reflux for 2 hours. The reaction solution was then distilled off under reduced pressure. The resulting residue was washed with water and recrystalized from methanol to obtain 12.8 g of 2-methyl-4-adamantyl-6-trichloromethyl-s-triazine in the form of a colorless solid.

5.2 g of 2-methyl-4-adamantyl-6-trichloromethyl-s-triazine thus obtained, 3.1 g of p-anisaldehyde, 2.2 g of piperidine acetate, and 15 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 1.1 g of Compound 75 in the form of a light yellow crystal having a melting point of 134° C.

$^1$HNMR(CDCl$_3$) δ(TMS, ppm ) 8.30 (1H, d), 7.66 (2H, d), 7.10 (1H, d), 6.97 (2H, d), 3.89 (3H, s), 2.20–2.10 (9H, brs), 1.85–1.80 (6H, brs).

UV spectrum (CH$_3$CN) $\lambda_{max}$349 nm (ε29600).

EXAMPLE 23

Synthesis of Compound 76

The same operation was conducted as in Example 22 except that 3.1 g of p-anisaldehyde was replaced by 4.4 g of p-methoxycarbonylmethoxybenzaldehyde. 0.26 g of Compound 76 was obtained in the form of a white crystal having a melting point of 150° C.

¹HNMR(CDCl₃) δ(TMS, ppm) 8.30 (1H, d), 7.65 (2H, d), 7.10 (2H, d), 6.95 (2H, d), 4.71 (2H, s), 3.84 (3H, s), 2.20–2.10 (9H, brs), 1.85–1.80 (6H, brs).

UV spectrum (CH₃CN) $\lambda_{max}$343 nm ($\epsilon$26800).

EXAMPLE 24

Synthesis of Compound 122

7.0 g of N-(acetymidyl)trichloroacetamidine, 10 g of triphenylacetylchloride, and 50 ml of toluene were mixed at 0° C. 4.8 ml of trimethylamine was added to the mixture, and then the mixture was heated under reflux for 2 hours. The reaction solution was distilled off under reduced pressure. The resulting residue was washed with water and then recrystalized from methanol to obtain 5.5 g of 2-methyl-4-triphenylmethyl-6-trichloromethyl-s-triazine in the form of a colorless solid.

3.2 g of 2-methyl-4-triphenylmethyl- 6-trichloromethyl-s-triazine thus obtained, 100 g of p-anisaldehyde, 1.0 g of piperidine acetate, and 7 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 0.15 g of Compound 122 in the form of a white crystal having a melting point of 140° C.

¹HNMR(CDCl₃) δ(TMS, ppm ) 8.13 (1H, d), 7.67 (2H, d), 7.32–7.20 (15H, m), 7.06 (1H, d), 6.94 (2H, d), 3.88 (3H, s).

UV spectrum (CH₃CN) $\lambda_{max}$358 nm ($\epsilon$29700).

EXAMPLE 25

Synthesis of Compound 135

6.12 g of N-(acetymidyl)trichloroacetamidine, 6.0 ml of benzoylchloride, and 120 ml of benzene were mixed. The mixture was heated under reflux for 2 hours. The reaction solution was distilled off under reduced pressure. The resulting residue was washed with water and then recrystalized from methanol to obtain 3.23 g of 2-methyl- 4-phenyl-6-trichloromethyl-s-triazine in the form of a colorless solid.

2.9 g of 2-methyl-4-phenyl-6-trichloromethyl-s-triazine thus obtained, 2.9 g of p-methoxycarbonylmethoxybenzaldeyde, 0.7 g of piperidine acetate, and 10 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 0.57 g of Compound 135 in the form of a white crystal having a melting point of 134°–135° C.

¹HNMR(CDCl₃) δ(TMS, ppm) 8.67 (2H, d), 8.40 (1H, d), 7.69 (2H, d), 7.65–7.52 (3H, m), 7.19 (1H, d), 6.98 (2H, d), 4.71 (2H, s), 3.83 (3H, s).

UV spectrum (CH₃CN) $\lambda_{max}$351 nm ($\epsilon$34000).

EXAMPLE 26

Synthesis of Compound 137

20.3 g of N-(acetymidyl)trichloroacetamidine, 14.4 ml of pentafluorobenzoylchloride, and 200 ml of benzene were mixed at 0° C. 13.9 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure. The resulting residue was recrystalized from methanol to obtain 23.0 g of 2-methyl-4-pentafluorophenyl-6-trichloromethyl-s-triazine in the form of a colorless liquid.

7.6 g of 2-methyl-4-pentafluorophenyl- 6-trichloromethyl-s-triazine thus obtained, 4.5 g of cuminaldehyde, 1.5 g of piperidine acetate, and 20 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 0.9 g of Compound 137 in the form of a light yellow crystal having a melting point of 132°–133° C.

¹HNMR(CDCl₃) δ(TMS, ppm) 8.43 (1H, d), 7.76 (2H, d), 7.33 (2H, d), 7.29 (1H, d), 2.97 (1H, dq), 1.30 (6H, d).

UV spectrum (CH₃CN) $\lambda_{max}$345 nm ($\epsilon$32500).

EXAMPLE 27

Synthesis of Compound 136

The same operation was conducted as in Example 26 except that 4.5 g of cuminaldehyde was replaced by 5.8 g of p-methoxycarbonylmethoxybenzaldehyde. 1.13 g of Compound 136 was obtained in the form of a light yellow crystal having a melting point of 112°–113° C.

¹HNMR(CDCl₃) δ(TMS, ppm ) 8.40 (1H, d), 7.69 (2H, d), 7.17 (1H, d), 6.98 (2H, d), 4.71 (2H, s), 3.84 (3H, s).

UV spectrum (CH₃CN) $\lambda_{max}$359 nm ($\epsilon$35800).

EXAMPLE 28

Synthesis of Compound 139

20.3 g of N-(acetymidyl)trichloroacetamidine, 12.0 ml of p-fluorobenzoylchloride, and 200 ml of benzene were mixed at 0° C. 13.9 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure to obtain 15.0 g of 2-methyl-4-(p-fluorophenyl)- 6-trichloromethyl-s-triazine in the form of a white solid. 7.1 g of 2-methyl-4-(p-fluorophenyl)- 6-trichloromethyl-s-triazine thus obtained, 4.5 g of cuminaldehylde, 1.5 g of piperidine acetate, and 20 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 0.7 g of Compound 139 in the form of a white crystal having a melting point of 127° C.

¹HNMR(CDCl₃) δ(TMS, ppm) 8.7o (2H, d), 8.40 (1H, d), 7.67 (2H, d), 7.31 (2H, d), 7.30–7.18 (3H, m), 2.97 (1H, dq), 1.30 (6H, d).

UV spectrum (CH₃CN) $\lambda_{max}$340 nm (ε31200).

EXAMPLE 29

Synthesis of Compound 140

The same operation was conducted as in Example 28 except that 4.5 g of cuminaldehyde was replaced by 5.8 g of P-methoxycarbonylmethoxybenzaldehyde. 1.3 g of Compound 140 was obtained in the form of a light yellow crystal having a melting point of 149°–150° C.

¹HNMR(CDCl₃) δ(TMS, ppm) 8.70 (1H, d), 8.67 (1H, d), 8.38 (1H, d), 7.69 (2H, d), 7.24 (2H, d), 6.98 (2H, d), 4.72 (2H, s), 3.85 (3H, s).

UV spectrum (CH₃CN) $\lambda_{max}$352 nm (ε32000).

EXAMPLE 30

Synthesis of Compound 141

20.3 g of N-(acetymidyl)trichloroacetamidine, 14.9 ml of p-trifluoromethylbenzoylchloride, and 200 ml of benzene were mixed at 0° C. 13.9 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure to obtain 27.5 g of 2-methyl- 4-(p-trifluoromethylphenyl)-6-trichloromethyl-s-triazine in the form of a white solid.

7.1 g of 2-methyl-4-(p-trifluoromethylphenyl)- 6-trichloromethyl-s-triazine thus obtained, 4.5 g of cuminaldehylde, 1.5 g of piperidine acetate, and 20 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 2.5 g of Compound 141 in the form of a white crystal having a melting point of 164° C.

¹HNMR(CDCl₃) δ(TMS, ppm) 8.78 (2H, d), 8.45 (1H, d), 7.82 (2H, d), 7.67 (2H, d), 7.33 (2H, d), 7.29 (1H, d), 2.98 (1H, dq), 1.30 (6H, d).

UV spectrum (CH₃CN) $\lambda_{max}$341 nm (ε35600).

EXAMPLE 31

Synthesis of Compound 142

The same operation was conducted as in Example 30 except that 4.5 g of cuminaldehyde was replaced by 4.2 g of p-chlorobenzaldehyde. 0.5 g of Compound 142 was obtained in the form of a white crystal having a melting point of 179°–180° C.

¹HNMR(CDCl₃) δ(TMS, ppm) 8.77 (2H, d), 8.40 (1H, d), 7.83 (2H, d), 7.68 (2H, d), 7.45 (2H, d), 7.30 (1H, d).

UV spectrum (CH₃CN) $\lambda_{max}$329 nm (ε34700).

EXAMPLE 32

Synthesis of Compound 143

20.3 g of N-(acetymidyl)trichloroacetamidine, 14.7 ml of o-trifluoromethylbenzoylchloride, and 200 ml of benzene were mixed at 0° C. 13.9 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure to obtain 22.4 g of 2-methyl- 4-(o-trifluoromethylphenyl)-6-trichloromethyl-s-triazine in the form of a white solid.

7.1 g of 2-methyl-4-(o-trifluoromethylphenyl)- 6-trichloromethyl-s-triazine thus obtained, 4.5 g of cuminaldehylde, 1.5 g of piperidine acetate, and 20 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 2.6 g of Compound 143 in the form of a light yellow liquid.

¹HNMR(CDCl₃) δ(TMS, ppm ) 8.43 (1H, d), 8.06 (1H, d), 7.90 (1H, d), 7.22 (2H, m), 7.30 (2H, d), 7.17 (1H, d), 2.97 (1H, dq), 1.30 (6H, d).

UV spectrum (CH₃CN) $\lambda_{max}$340 nm (ε40200)

EXAMPLE 33

Synthesis of Compound 144

The same operation was conducted as in Example 32 except that 4.5 g of cuminaldehyde was replaced by 5.8 g of p-methoxycarbonylmethoxybenzaldehyde. 4.0 g of Compound 144 was obtained in the form of a light yellow crystal having a melting point of 99°–100° C.

¹HNMR(CDCl₃) δ(TMS, ppm) 8.40 (1H, d), 8.05 (1H, d), 7.90 (1H, d), 7.22 (2H, m), 7.17 (1H, d), 6.98 (2H, d), 4.70 (2H, s), 3.83 (3H, s).

UV spectrum (CH₃CN) $\lambda_{max}$354 nm (ε32300).

EXAMPLE 34

Synthesis of Compound 147

20.3 g of N-(acetymidyl)trichloroacetamidine, 18.6 g of p-nitrobenzoylchloride, and 200 ml of benzene were mixed at 0° C. 13.9 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure to obtain 13.9 g of 2-methyl-4-(p-nitrophenyl)- 6-trichloromethyl-s-triazine in the form of a light yellow liquid. 6.7 g of 2-methyl-4-(p-nitrophenyl)- 6-trichloromethyl-s-triazine thus obtained, 4.5 g of cuminaldehylde, 1.5 g of piperidine acetate, and 20 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 0.7 g of Compound 147 in the form of a redish brown crystal having a melting point of 168°–169° C.

¹HNMR(CDCl3) δ(TMS, ppm) 8.83 (2H, d), 8.47 (1H, d), 8.40 (2H, d), 7.69 (2H, d), 7.34 (2H, d), 7.30 (1H, d), 2.98 (1H, dq), 1.30 (6H, d).

UV spectrum (CH$_3$CN) $\lambda_{max}$342 nm (ε31700).

EXAMPLE 35

Synthesis of Compound 148

20.3 g of N-(acetymidyl)trfchloroacetamidine, 17.1 g of p-methoxybenzoylchloride, and 200 ml of benzene were mixed at 0° C. 13.9 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure to obtain 12.7 g of 2-methyl-4-(p-methoxyphenyl)-6-trichloromethyl-s-triazine in the form of a light yellow liquid. 4.8 g of 2-methyl-4-(p-methoxyphenyl)- 6-trichloromethyl-s-triazine thus obtained, 3.3 g of cuminaldehyde, 1.1 g of piperidine acetate, and 15 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 0.8 g of Compound 148 in the form of a white crystal having a melting point of 136°–137° C.

¹HNMR(CDCl$_3$) δ(TMS, ppm) 8.62 (2H, d), 8.39 (1H, d), 7.65 (2H, d), 7.30 (2H, d), 7.23 (1H, d), 7.05 (2H, d), 3.91 (3H, s° ), 2.96 (1H, dq), 1.30 (6H, d).

UV spectrum (CH$_3$CN) $\lambda_{max}$334 nm (ε48200).

EXAMPLE 36

Synthesis of Compound 149

The same operation was conducted as in Example 35 except that 3.3 g of cuminaldehyde was replaced by 4.4 g of p-methoxycarbonylmethoxybenzaldehyde. 1.31 g of Compound 149 was obtained in the form of a white crystal having a melting point of 154°–155° C.

¹HNMR(CDCl$_3$) δ(TMS, ppm) 8.62 (2H, d), 8.35 (1H, d), 7.67 (2H, d), 7.15 (1H, d), 7.04 (2H, d), 6.97 (2H, d), 4.70 (2H, s), 3.91 (3H, s), 3.83 (3H, s).

UV spectrum (CH$_3$CN) $\lambda_{max}$347 nm (ε38100).

EXAMPLE 37

Synthesis of Compound 152

20.3 g of N-(acetymidyl)trichloroacetamidine, 16.6 g of p-cyanobenzoylchloride, and 200 ml of benzene were mixed at 0° C. 13.9 ml of trimethylamine was added to the mixture, and then the mixture was heated under reflux for 2 hours. The reaction solution was then extracted with ethyl acetate. The ethyl acetate solution thus extracted was washed with water, and then distilled off under reduced pressure to obtain 17.1 g of 2-methyl-4-(p-cyanophenyl)- 6-trichloromethyl-s-triazine in the form of a white solid.

6.3 g of 2-methyl-4-(p-cyanophenyl)- 6-trichloromethyl-s-triazine thus obtained, 4.5 g of cuminaldehylde, 1.5 g of piperidine acetate, and 20 ml of toluene were mixed. The mixture was heated under reflux for hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 1.0 g of Compound 152 in the form of a white crystal having a melting point of 170° C.

¹HNMR(CDCl$_3$) δ(TMS, ppm ) 8.80 (2H, d), 8.45 (1n, d), 7.87 (2H, d), 7.68 (2H, d), 7.35 (2H, d), 7.30 (1H, d), 2.98 (1H, dq), 1.30 (6H, d).

UV spectrum (CH$_3$CN) $\lambda_{max}$341 nm (ε25500).

EXAMPLE 38

Synthesis of Compound 154

The same operation was conducted as in Example 37 except that 4.5 g of cuminaldehyde was replaced by 5.8 g of p-methoxycarbonylmethoxybenzaldehyde. 1.2 g of Compound 154 was obtained in the form of a light yellow crystal having a melting point of 186°–188° C.

¹HNMR(CDCl$_3$) δ(TMS, ppm ) 8.8o (2H, d), 8.42 (1H, d), 7.86 (2H, d), 7.70 (2H, d), 7.20 (1H, d), 7.00 (2H, d), 4.73 (2H, s), 3.85 (3H, s).

UV spectrum (CH$_3$CN) $\lambda_{max}$356 nm (ε29600).

EXAMPLE 39

Synthesis of Compound 165

20.3 g of N-(acetymidyl)trichloroacetamidine, 19.6 g of maleic anhydride, and 200 ml of toluene were mixed, and the mixture was heated under reflux for 4 hours. The reaction solution was then distilled off under reduced pressure, followed by being washed with water, to obtain 21.4 g of 2-methyl-4-carboxyvinyl-6-trichloromethyl-s-triazine in the form of a white solid.

21.4 g of 2-methyl-4-carboxyvinyl-6-trichloromethyl-s-triazine thus obtained, 9.3 ml of boron trifluoride diethylether complex, and 100 ml of methanol were mixed. The mixture was heated under reflux for 11 hours. The reaction solution was then extracted with ethyl acetate. The ethyl acetate solution thus extracted wag washed with water, and then distilled off under reduced pressure. The resulting residue was purified through column chromatography to obtain 4.5 g of 2-methyl-4-methoxycarbonylvinyl-6-trichloromethyl-s-triazine in the form of a white solid.

3.0 g of 2-methyl-4-methoxycarbonylvinyl- 6-trichloromethyl-s-triazine thus obtained, 2.3 g of cuminaldehylde, 1.5 g of piperidine acetate, and 10 ml of toluene were mixed. The mixture was heated under reflux for 10 hours while released water was being recovered by Dean-Stark's extractor. The reaction solution was then extracted with ethyl acetate. The ethyl acetate solution thus extracted was washed with water, and then distilled off under reduced pressure. The resulting residue was purified through column chromatography to obtain 1.6 g of Compound 165 in the form of a light yellow crystal having a melting point of 103°–104° C.

¹HNMR(CDCl$_3$) δ(TMS, ppm) 8.38 (1H, d), 7.68 (1H, d), 7.64 (2H, d), 7.51 (1H, d), 7.31 (2H, d), 7.21 (1H, d), 3.89 (3H, s), 2.67 (1H, dq), 1.30 (6H, d).

UV spectrum (CH$_3$CN) $\lambda_{max}$340 nm (ε26200).

EXAMPLES 40 THROUGH 96

It was demonstrated that the compounds according to the present invention are useful in the reduction of coloration of products of decomposition by exposure to light and coloration due to exposure to light during storage in bright places.

1. Preparation of photosensitive liquid for photopolymerizable composition and formation of photosensitive layer A mother liquor having the following formulation A was prepared.

Formulation A:

| | |
|---|---|
| Benzyl methacrylate/methacrylic acid copolymer (copolymerization composition ratio (molar ratio) = 7/27; viscosity: 0.12) | 144 g |
| Pentaerythritol tetraacrylate | 144 g |
| Fluorine surface active agent (Megafac F-176PF, available from Dainippon Ink & Chemicals, Inc.) | 1.4 g |
| Methylcellosolve acetate | 292 g |
| Methyl ethyl ketone | 252 g |
| 1-Methoxy-2-propyl acetate | 126 g |

To 90 g of the mother liquor thus obtained was added 1.55 mol of the compounds set forth in Table 1, respectively, to make solutions as photosensitive coating solutions. These photosensitive coating solutions were each applied to a 100-μm thick polyethylene terephthalate film by means of a spin coater to a dry thickness of 10 μm, and then dried to form photosensitive layers.

2. Preparation of coating solution for protective layer and formation of protective layer The photosensitive layers were each coated with a coating solution having the following formulation B to a dry thickness of 1.5 μm by means of a spin coater, and then dried.

Formulation B:

| | |
|---|---|
| Polyvinyl alcohol (PVA205, available from Kuraray Co., Ltd.; percent saponification: 80%) | 130 parts |
| Polyvinyl pyrrolidone (PVPK-90, available from GAF Corporation) | 60 parts |
| Fluorine surface active agent (Surflon S-131, available from Asahi Glass Co., Ltd.) | 10 parts |
| Distilled water | 3,350 parts |

3. Evaluation of photosensitive material

3-1. Sensitivity test

The samples thus obtained were each exposed to light from a 1.5-kW ultrahigh voltage mercury vapor lamp P-627GM (available from Dainippon Screen Mfg. Co., Ltd.) through a step wedge (density difference: 0.15; number of density steps: 15; Fuji Step Guide-P, available from Fuji Photo Film Co., Ltd.) for 24 seconds, and then subjected to automatic development with a developer obtained by diluting a color art developer CA-1 (trade name manufactured by Fuji Photo Film Co., Ltd.) by a factor of 5 at a temperature of 32° C. for 38 seconds (using a color art processor CA-600P, available from Fuji Photo Film Co., Ltd.). The highest number of steps at which no film thickness change occurs as determined by means of a film thickness gauge (Alpha Step 200, available from Tencor Instruments Co., Ltd.) was determined as a solid step. This step number was regarded as the sensitivity.

3-2. Imagewise exposure coloration test

The samples were each exposed to light from a 1.5-kW ultrahigh voltage mercury vapor lamp P-627 GM (manufactured by Dainippon Screen Mfg. Co., Ltd.) on the coated surface thereof for 240 seconds, and then measured for coloration by means of a transmission densitometer TD904 (using Y filter; manufactured by Macbeth Co., Ltd.). The value obtained with the unexposed specimen was subtracted from the value thus obtained to determine the degree of imagewise exposure coloration.

3-3. Prolonged exposure coloration test

The samples were each exposed to light from a 1.5-kW ultrahigh voltage mercury vapor lamp P-627 GM (manufactured by Dainippon Screen Mfg. Co., Ltd.) for 240 seconds and then to light from a 0.08 W/m² xenon lamp (WEATHER-OMETER; ModelC-165; available from Atlas Electric Devices Co., Ltd.) for 6 hours, and then measured for coloration by means of a transmission densitometer TD904 (using Y filter; manufactured by Macbeth Co., Ltd.). The value obtained with the unexposed specimen was subtracted from the value thus obtained to determine the degree of coloration due to prolonged exposure.

COMPARATIVE EXAMPLES 1 THROUGH 9

Samples were obtained in the same manner as in Example 40 except that the radical photopolymerization initiator to be used in the preparation of the photosensitive layer was replaced by the comparative compounds as set forth below, respectively. These samples were evaluated in the same manner as in Example 40.

TABLE 1

(Radical polymerization initiator used in the preparation of photosensitive layer)

| Example No. | Radical photopolymerization initiator |
|---|---|
| Example 40 | Compound 1 |
| Example 41 | Compound 2 |
| Example 42 | Compound 3 |
| Example 43 | Compound 5 |
| Example 44 | Compound 22 |
| Example 45 | Compound 28 |
| Example 46 | Compound 60 |
| Example 47 | Compound 79 |
| Example 48 | Compound 128 |
| Example 49 | Compound 134 |

TABLE 1-continued (Radical polymerization initiator used in the preparation of photosensitive layer)

| Example No. | Radical photopolymerization initiator |
| --- | --- |
| Example 50 | Compound 147 |
| Example 51 | Compound 150 |
| Example 52 | Compound 9 |
| Example 53 | Compound 14 |
| Example 54 | Compound 18 |
| Example 55 | Compound 35 |
| Example 56 | Compound 61 |
| Example 57 | Compound 62 |
| Example 58 | Compound 70 |
| Example 59 | Compound 71 |
| Example 60 | Compound 96 |
| Example 61 | Compound 103 |
| Example 62 | Compound 106 |
| Example 63 | Compound 107 |
| Example 64 | Compound 111 |
| Example 65 | Compound 118 |
| Example 66 | Compound 122 |
| Example 67 | Compound 125 |
| Example 68 | Compound 139 |
| Example 69 | Compound 142 |
| Example 70 | Compound 143 |
| Example 71 | Compound 148 |
| Example 72 | Compound 152 |
| Example 73 | Compound 165 |
| Example 74 | Compound 7 |
| Example 75 | Compound 13 |
| Example 76 | Compound 54 |
| Example 77 | Compound 66 |
| Example 78 | Compound 75 |
| Example 79 | Compound 76 |
| Example 80 | Compound 88 |
| Example 81 | Compound 91 |
| Example 82 | Compound 93 |
| Example 83 | Compound 95 |
| Example 84 | Compound 119 |
| Example 85 | Compound 129 |
| Example 86 | Compound 135 |
| Example 87 | Compound 136 |
| Example 88 | Compound 137 |
| Example 89 | Compound 140 |
| Example 90 | Compound 141 |
| Example 91 | Compound 144 |
| Example 92 | Compound 149 |
| Example 93 | Compound 153 |
| Example 94 | Compound 154 |
| Example 95 | Compound 163 |
| Example 96 | Compound 164 |
| Comparative Example 1 | NC—C$_6$H$_4$—CH=CH—[triazine with two CCl$_3$ groups] |
| Comparative Example 2 | MeO—C$_6$H$_4$—[triazine with NH—CO—OCH$_2$CH$_2$O—CO—CH=CH$_2$ and CCl$_3$] |
| Comparative Example 3 | C$_6$H$_5$—CH=CH—[triazine with two CCl$_3$ groups] |

TABLE 1-continued (Radical polymerization initiator used in the preparation of photosensitive layer)

| Example No. | Radical photopolymerization initiator |
|---|---|
| Comparative Example 4 | 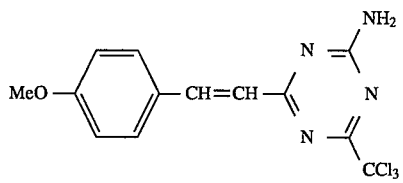 |
| Comparative Example 5 | 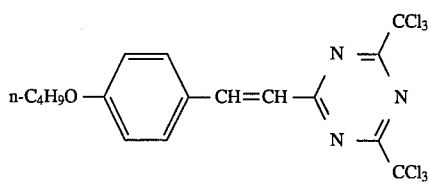 |
| Comparative Example 6 | 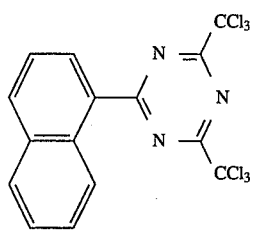 |
| Comparative Example 7 | 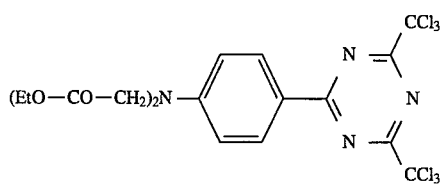 |
| Comparative Example 8 | 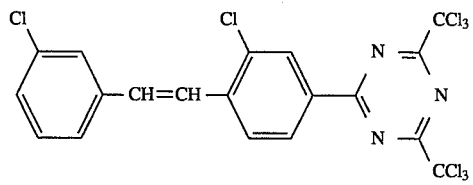 |
| Comparative Example 9 | 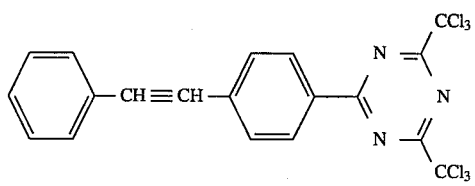 |

Method of Comparison:

The comparison of the degree of exposure coloration was made with compounds having almost the same sensitivity. The compounds having a sensitivity ranging from Step 1 to Step 4 were grouped as Group A. The compounds having a sensitivity ranging from Step 5 to Step 7 were grouped as Group B. The compounds having a sensitivity ranging from Step 8 to Step 10 were grouped as Group C. The results of evaluation of the compounds belonging to Group A, Group B and Group C are set forth in Tables 2, 3 and 4, respectively.

TABLE 2

(Results of evaluation of compounds of Group A)

| Example No. | Sensitivity | Exposure coloration | Prolonged exposure coloration |
|---|---|---|---|
| Example 40 | Step 1 | 0.00 | 0.00 |
| Example 41 | Step 4 | 0.00 | 0.01 |
| Example 42 | Step 4 | 0.00 | 0.01 |
| Example 43 | Step 4 | 0.00 | 0.01 |
| Example 44 | Step 2 | 0.00 | 0.00 |
| Example 45 | Step 2 | 0.00 | 0.00 |
| Example 46 | Step 4 | 0.00 | 0.01 |

TABLE 2-continued (Results of evaluation of compounds of Group A)

| Example No. | Sensitivity | Exposure coloration | Prolonged exposure coloration |
|---|---|---|---|
| Example 47 | Step 2 | 0.00 | 0.00 |
| Example 48 | Step 4 | 0.00 | 0.00 |
| Example 49 | Step 1 | 0.00 | 0.00 |
| Example 50 | Step 3 | 0.00 | 0.01 |
| Example 51 | Step 4 | 0.00 | 0.01 |
| Comparative Example 1 | Step 1 | 0.01 | 0.02 |
| Comparative Example 2 | Step 4 | 0.02 | 0.03 |

TABLE 3

(Results of evaluation of compounds of Group B)

| Example No. | Sensitivity | Exposure coloration | Prolonged exposure coloration |
|---|---|---|---|
| Example 52 | Step 5 | 0.00 | 0.01 |
| Example 53 | Step 5 | 0.00 | 0.01 |
| Example 54 | Step 7 | 0.00 | 0.01 |
| Example 55 | Step 5 | 0.00 | 0.02 |
| Example 56 | Step 7 | 0.00 | 0.01 |
| Example 57 | Step 7 | 0.00 | 0.01 |
| Example 58 | Step 7 | 0.00 | 0.02 |
| Example 59 | Step 7 | 0.00 | 0.02 |
| Example 60 | Step 5 | 0.00 | 0.01 |
| Example 61 | Step 6 | 0.00 | 0.01 |
| Example 62 | Step 6 | 0.00 | 0.00 |
| Example 63 | Step 6 | 0.00 | 0.01 |
| Example 64 | Step 6 | 0.00 | 0.01 |
| Example 65 | Step 6 | 0.00 | 0.01 |
| Example 66 | Step 7 | 0.00 | 0.02 |
| Example 67 | Step 7 | 0.00 | 0.01 |
| Example 68 | Step 5 | 0.00 | 0.01 |
| Example 69 | Step 5 | 0.00 | 0.01 |
| Example 70 | Step 7 | 0.00 | 0.02 |
| Example 71 | Step 7 | 0.00 | 0.02 |
| Example 72 | Step 7 | 0.00 | 0.02 |
| Example 73 | Step 7 | 0.00 | 0.02 |
| Comparative Example 3 | Step 7 | 0.01 | 0.03 |
| Comparative Example 4 | Step 7 | 0.03 | 0.05 |

TABLE 4

(Results of evaluation of compounds of Group C)

| Example No. | Sensitivity | Exposure coloration | Prolonged exposure coloration |
|---|---|---|---|
| Example 74 | Step 8 | 0.02 | 0.02 |
| Example 75 | Step 8 | 0.01 | 0.01 |
| Example 76 | Step 9 | 0.02 | 0.02 |
| Example 77 | Step 8 | 0.02 | 0.02 |
| Example 78 | Step 8 | 0.02 | 0.02 |
| Example 79 | Step 8 | 0.01 | 0.01 |
| Example 80 | Step 9 | 0.01 | 0.02 |
| Example 81 | Step 9 | 0.02 | 0.01 |
| Example 82 | Step 10 | 0.02 | 0.02 |
| Example 83 | Step 9 | 0.01 | 0.02 |
| Example 84 | Step 9 | 0.01 | 0.02 |
| Example 85 | Step 9 | 0.01 | 0.02 |
| Example 86 | Step 8 | 0.01 | 0.02 |
| Example 87 | Step 9 | 0.01 | 0.02 |

TABLE 4-continued (Results of evaluation of compounds of Group C)

| Example No. | Sensitivity | Exposure coloration | Prolonged exposure coloration |
|---|---|---|---|
| Example 88 | Step 10 | 0.02 | 0.03 |
| Example 89 | Step 9 | 0.01 | 0.02 |
| Example 90 | Step 9 | 0.01 | 0.02 |
| Example 91 | Step 9 | 0.01 | 0.01 |
| Example 92 | Step 9 | 0.02 | 0.03 |
| Example 93 | Step 9 | 0.01 | 0.02 |
| Example 94 | Step 9 | 0.01 | 0.03 |
| Example 95 | Step 8 | 0.01 | 0.01 |
| Example 96 | Step 8 | 0.01 | 0.01 |
| Comparative Example 5 | Step 10 | 0.03 | 0.05 |
| Comparative Example 6 | Step 9 | 0.03 | 0.04 |
| Comparative Example 7 | Step 10 | 0.03 | 0.05 |
| Comparative Example 8 | Step 10 | 0.03 | 0.04 |
| Comparative Example 9 | Step 9 | 0.03 | 0.04 |

The results in Tables 2, 3 and 4 show that the compounds of the present invention exhibit a lesser degree of exposure coloration and prolonged exposure coloration than the comparative compounds which have almost the same sensitivity as the compounds of the present invention.

The trihalomethyl-s-triazine compound of the present invention is remarkably insusceptible to coloration of itself and decomposition products. The use of this compound can provide a photopolymerizable composition which is less liable to exposure coloration upon imagewise exposure and during storage in bright places.

While the invention has been described in detail and with reference to specific embodiments thereof, it will be apparent to one skilled in the art that various changes and modifications can be made therein Without departing from the spirit and scope thereof.

What is claimed is:

1. A photosensitive trihalomethyl-s-triazine compound, represented by formula (I):

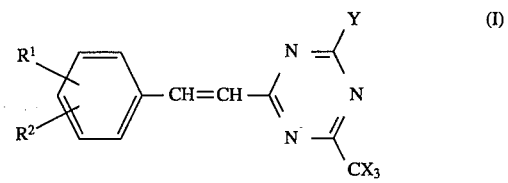

wherein X represents a chlorine atom or a bromine atom; Y represents an alkyl group, a $CF_3$ group, a $CF_2Cl$ group, an alkyl group substituted with a group or an atom other than hydrogen atoms, a $C_6F_5$ group, or a group represented by $-Z-CO-OR^3$ or $-C_6H_4-R^4$, in which $R^3$ represents a hydrogen atom or alkyl group, Z represents $-C_2H_4-$, $-C_3H_6-$, $-CH=CH-$, or o-phenylene group, and $R^4$ represents a hydrogen atom, a hydroxyl group, an alkyl group, a substituted alkyl group, an aryl group, an alkoxy group, a substituted alkoxy group, a halogen atom, an alkoxycarbonyl group, a cyano group, an acyl group, a nitro group, a formyl group, a mercapto group, an alkylthio group, or a dialkylamino group; $R^1$ and $R^2$ each independently represent a hydrogen atom, a hydroxyl group, an alkyl group, an aryl group, an alkoxy group, a substituted alkoxy group, an acyloxy group, a halogen atom, an alkoxycarbonyl group, a cyano group, a nitro group, a carboxyl group, or a group represented by formula (II) or (III):

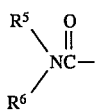 (II)

wherein $R^5$ and $R^6$ each independently represent a hydrogen atom, an alkyl group, a substituted alkyl group, or a substituted aryl group,

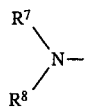 (III)

wherein $R^7$ and $R^8$ each independently represent a hydrogen atom, an alkyl group, a substituted alkyl group, an aryl group, a substituted aryl group, of an acyl group, and wherein $R^5$ and $R^7$ may be connected to $R^6$ and $R^8$, respectively, to form a ring.

2. A photosensitive trihalomethyl-s-triazine compound as claimed in claim 1, wherein X represents a chlorine atom; Y represents a methyl group, an ethyl group, a $CF_3$ group, a carboxylethyl group, a methoxycarbonylethyl group, a methoxycabonylpropyl group, a phenyl group, a p-cyanophenyl group, or a p-methoxyphenyl group; and $R^1$ and $R^2$ each independently represent a hydrogen atom, a halogen atom, a methyl group, an ethyl group, an isopropyl group, a methoxy group, an ethoxy group, an isopropoxy group, a butoxy group, a methoxycarbonylmethoxy group, an ethoxycarbonylmethoxy group, a cyanomethoxy group, a cyanoethoxy group, an acetoxy group, a benzoyloxy group, a phenylaminocarbonyl group, an anisylaminocarbonyl group, a diphenylaminocarbonyl group, a dianisylaminocarbonyl group, a dimethylaminocarbonyl group, a diethylaminocarbonyl group, an acetylamino group, or a benzoylamino group.

* * * * *